United States Patent [19]

Machida et al.

[11] 4,285,941
[45] Aug. 25, 1981

[54] CEPHALOSPORIN COMPOUNDS AND ANTIBACTERIAL DRUGS CONTAINING THE SAME

[75] Inventors: Yoshimasa Machida, Wako; Isao Saito, Chofu; Seiichiro Nomoto, Tokyo; Shigeto Negi, Kodaira; Takeo Kanai, Honjo; Kyosuke Kitoh, Kawagoe; Kanemasa Katsu, Chofu; Yukio Ohya, Koganei; Takeshi Nagasu, Tokyo, all of Japan

[73] Assignee: Eisai Co., Ltd., Tokyo, Japan

[21] Appl. No.: 142,160

[22] Filed: Apr. 14, 1980

[30] Foreign Application Priority Data

Jun. 26, 1979 [JP] Japan .................. 54/79631

[51] Int. Cl.³ .......................... C07D 501/36
[52] U.S. Cl. ........................ 424/246; 544/27
[58] Field of Search ............ 544/30, 26, 27, 28; 424/246

[56] References Cited

U.S. PATENT DOCUMENTS

| 4,015,000 | 3/1977 | Kocsis et al. | 544/26 |
| 4,101,661 | 7/1978 | Kaltenbronn et al. | 544/26 |

Primary Examiner—Nicholas S. Rizzo

Attorney, Agent, or Firm—Wenderoth, Lind & Ponack

[57] ABSTRACT

Novel cephalosporin compounds of the general formula:

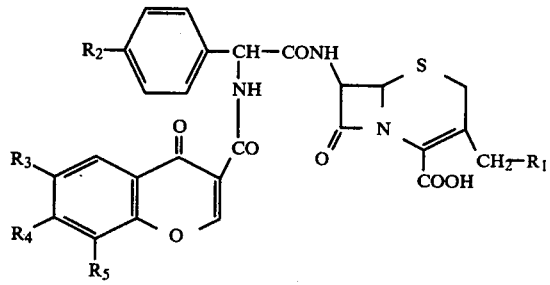

wherein $R_1$ represents a substituted or unsubstituted nitrogen-containing heterocyclic-thio group, $R_2$ represents hydrogen or hydroxy, and $R_3$, $R_4$ and $R_5$ each represents hydrogen, hydroxy or acyloxy, and their salts, and processes for the preparation thereof. The novel compounds and their salts have antibacterial activity.

17 Claims, No Drawings

CEPHALOSPORIN COMPOUNDS AND ANTIBACTERIAL DRUGS CONTAINING THE SAME

This invention relates to novel cephalosporin compounds as represented by the general formula:

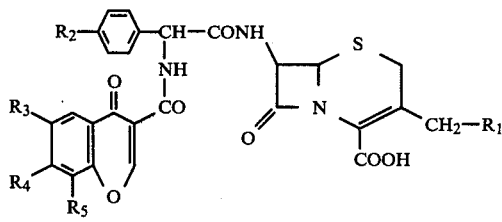

wherein $R_1$ is a substituted or unsubstituted nitrogen-containing heterocyclic-thio group, $R_2$ is hydrogen or hydroxy, $R_3$, $R_4$ and $R_5$ each is hydrogen, hydroxy, or acyloxy, or their salts, the processes for the preparation thereof, and antibacterial drugs containing these compounds.

There have been known, as compounds represented by the general formula:

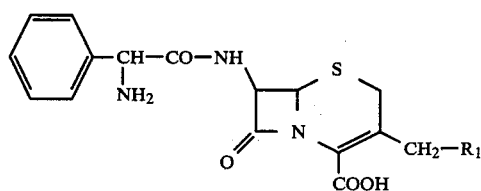

wherein $R_1$ is hydrogen or acyloxy, "Cephalexin" which was disclosed in Belgian Pat. No. 696,026 (1967) and "Cephaloglycine" which was disclosed in Belgian Patent No. 635,137 (1964), and the like.

The said substituted or unsubstituted nitrogen-containing heterocyclic-thio group which is represented by $R_1$ in the general formula (I) means a substituted or unsubstituted heterocyclic-thio group containing one or more nitrogen atoms as hetero atoms. The said nitrogen-containing heterocyclic group may be a mono- or polycyclic group. These nitrogen-containing heterocyclic groups may contain one or more nitrogen atoms only as hetero atom or atoms, or they may also contain other hetero atom or atoms such as sulfur and oxygen in addition to nitrogen. Representative of such nitrogen-containing heterocyclic groups are, for example, pyrrolyl, pyridyl and its N-oxide, imidazolyl, pyrazolyl, pyrimidinyl, pyridazinyl, 1H-1,2,4-triazolyl, 4H-1,2,4-triazolyl, 1H-1,2,3-triazolyl, 2H-1,2,3-triazolyl, 1H-tetrazolyl, 2H-tetrazolyl, thiazolyl, 1,2,3-thiadiazolyl, 1,2,4-thiadiazolyl, 1,3,4-thiadiazolyl, oxazolyl, 1,3,4-oxadiazolyl, 1,2,5-oxadiazolyl, morpholino, benzothiazolyl, benzoxazolyl, and the like. These groups may have one or more substituents. The examples of such substituents are alkyl groups such as methyl, ethyl, propyl, isopropyl and the like; amino groups; dialkylaminoalkyl groups such as dimethylaminoethyl, dimethylaminomethyl, diethylaminoethyl, and the like, and carboxyalkyl groups such as carboxymethyl, carboxyethyl, and the like.

Representative of the said acyloxy groups as $R_3$, $R_4$ and $R_5$ are acetoxy, propionyloxy, benzoyloxy, and the like.

Representative of the salts of the cephalosporin compounds of the general formula (I) are sodium salts, potassium salts, calcium salts, ammonium salts, triethylamine salts, dicyclohexylamine salts, procaine salts, and the like. The term "salts" generally refers to the carboxylate salts but, when $R_4$ in the general formula (I) is hydroxy, the term may refer to the carboxylate salts in which $R_4$ is or is not converted into a phenolate type functional group such as sodiooxy or potassiooxy.

The compounds of this invention are prepared by any one of the following methods:

Method A

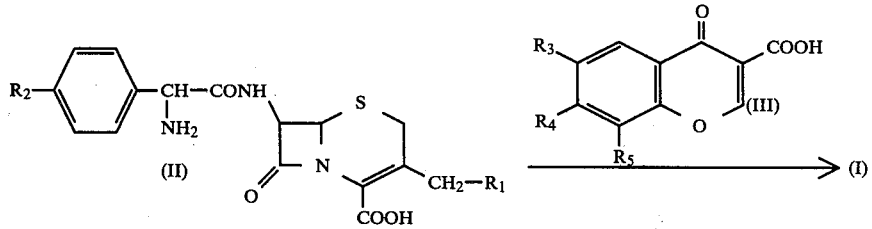

wherein $R_1$, $R_2$, $R_3$, $R_4$ and $R_5$ are as previously defined hereinbefore.

The compounds of this invention can be obtained by reacting the compounds (III) or their reactive derivatives at the carboxyl group thereof with the compounds (II) or their salts.

When the compounds (II) as free carboxylic acids (-COOH) are used for the said reaction, it is preferred to effect the reaction in the presence of a condensation agent, such as N,N'-dicyclohexyl carbodiimide, N,N'-diethylcarbodiimide, N-cyclohexyl-N'-morpholinoethylcarbodiimide, trialkyl phosphite, ethyl polyphosphate, phosphorus oxychloride, oxalyl chloride, and the like.

The representative examples of the reactive derivatives of (III) are acid halides such as acid chlorides, acid bromides, and the like; a symmetrical acid anhydride; a mixed anhydride derived from chlorocarbonate ester, trimethylacetic acid, thioacetic acid, diphenylacetic acid, and the like; a reactive ester derived from 2-mercaptopyridine, cyanomethanol, p-nitrophenol, 2,4-dinitrophenol, pentachlorophenol, and the like; a reactive acid amide, such as, N-acylsaccharin, N-acylphthalimide, and the like.

The said N-acylation reaction can be achieved in an inert solvent at temperatures from −50° to 50° C., preferably from −20° C. to 30° C., in the presence or absence of a basic reagent or silylating reagent. Representative of the said inert solvents are acetone, tetrahydrofuran, dimethylacetamide, dimethylformamide, dioxane, dichloromethane, chloroform, benzene, toluene, ethyl acetate and the mixture thereof.

Representative of the said basic reagents are, alkali hydroxides such as sodium hydroxide, potassium hydroxide, and the like; alkali hydrogen carbonates such as potassium hydrogen carbonate, sodium hydrogen carbonate and the like; amines such as triethylamine, pyridine, dimethylaniline, N-methylmorpholine, and the like.

Examples of the said silylating reagents are N,O-bis (trimethylsilyl) acetamide, hexamethyldisilazane, N-trimethylsilylacetamide, and the like.

The starting materials (III) for use in the process of this embodiment of the invention may be prepared by oxidizing the corresponding chromone aldehydes with Jones reagent (see Reagents for Organic Synthesis, Vol. 1, P. 142). When the substituents of the compounds (III) are hydroxy, the compounds (III) can also be provided by oxidizing the chromone aldehydes which have acyloxy in place of hydroxy according to the method described above to form the chromone carboxylic acids, followed by hydrolysis of the said chromone carboxylic acids.

The acid halides of the compounds (III) can be produced by reacting the compounds (III) with a halogenating reagent such as phosphorus pentachloride, thionyl chloride, and the like. The said chromone aldehydes can be produced by a conventional process, such as the process described in Tetrahedron, 30, 3553 (1974).

The compounds (II), which are also the starting materials of the compounds of this invention, can be prepared according to the process described in The Journal of Antibiotics 29, 65 (1976).

The compounds of this invention can also be prepared by the following methods.

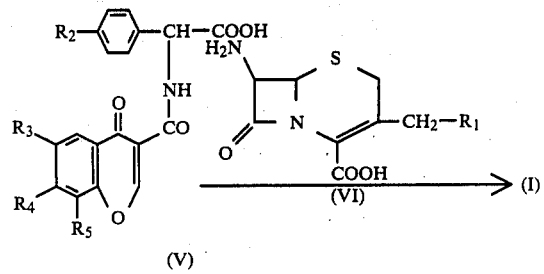

Method D

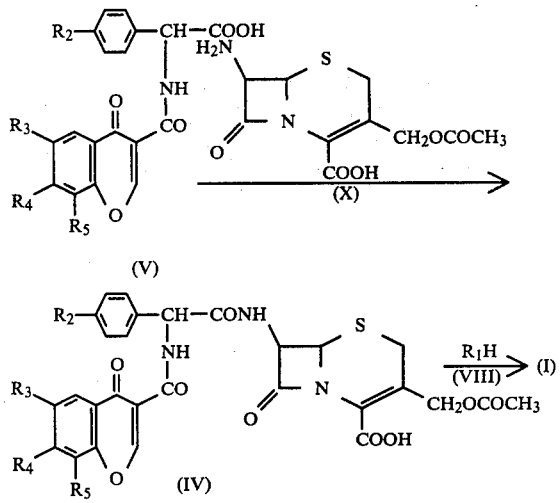

Method B

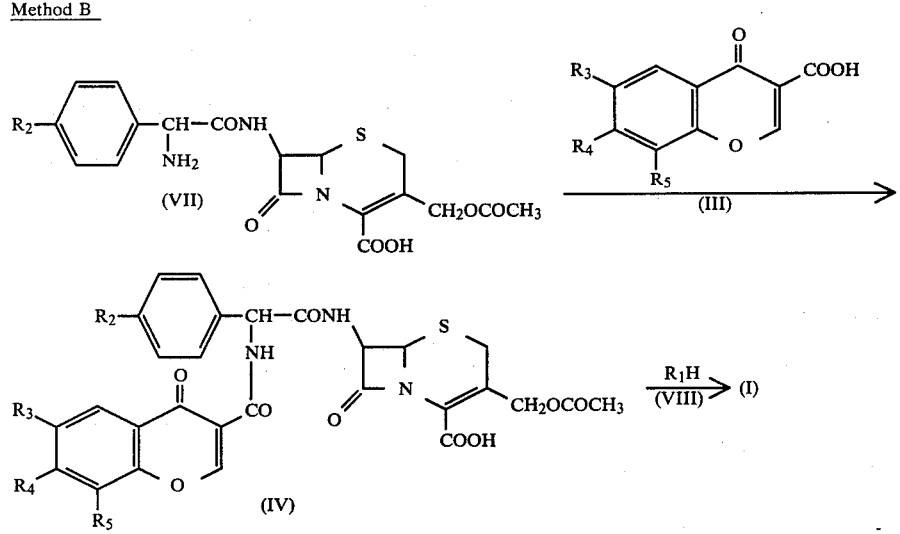

Method C

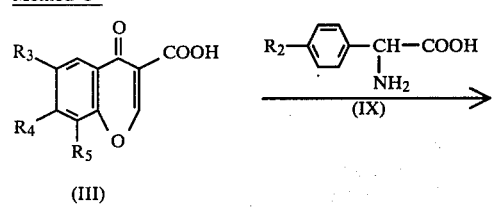

wherein $R_1$, $R_2$, $R_3$, $R_4$ and $R_5$ are as previously defined hereinbefore.

N-acylation reaction in Methods B, C and D can be effected basically in the same manner as that of Method A. The reaction between the compounds (IV) and the compounds (VIII) in Methods B and D can be effected in a solvent, such as, water, a buffer solution, and the like, at temperatures from 50° C. to 70° C. in the presence of a basic reagent, such as sodium hydrogen carbonate, sodium hydroxide, and the like. The compounds (I) containing hydroxy as substituent on the chromone moiety may be prepared by any one of the Methods A to D using the starting materials containing hydroxy. Alternatively, when starting materials containing the acyloxy group are used, the compounds (I) may be prepared by hydrolyzing the acyloxy groups in one of the intermediate steps or in the final step of the said processes.

Representative of this invention are the following compounds and their sodium salts:

7β-[D-2-(6,7-dihydroxychromone-3-carboxamido)-2-phenylacetamido]-3-[(5-methyl-1,3,4-thiadiazol-2-yl)thiomethyl]-3-cephem-4-carboxylic acid, 7β-[D-2-(6,7-Dihydroxy-chromone-3-carboxamido)-2-phenylacetamido]-3-[(1-methyltetrazol-5-yl)thiomethyl]-3-cephem-4-carboxylic acid, 7β-[D-2-(6,7-Dihydroxychromone-3-carboxamido)-2-phenylacetamido]-3[(1,3,4-thiadiazol-2-yl)thiomethyl]-3-cephem-4-carboxylic acid, 7β-[D-2-(6,7-Dihydroxychromone-3-carboxamido)-2-phenylacetamido]-3-[(1-(2-dimethylaminoethyl)tetrazol-5-yl]-thiomethyl]-3-cephem-4-carboxylic acid, 7β-[D-2-(6,7-Dihydroxychromone-3-carboxamido)-2-phenylacetamido]-3-[(1H-1,2,3-triazol-5-yl)thiomethyl]-3-cephem-4-carboxylic acid, 7β-[D-2-(6,7-Dihydroxy-chromone-3-carboxamido)-2-phenylacetamido]-3-[(5-methyl-1,3,4-oxadiazol-2-yl)-thiomethyl]-3-cephem-4-carboxylic acid, 7β-[D-2-(6,7-dihydroxychromone-3-carboxamido)-2-phenylacetamido]-3-[2-(pyridyl-1-oxido)thiomethyl]-3-cephem-4-carboxylic acid, 7β-[D-2-(6,7-Dihydroxychromone-3-carboxamido)-2-phenylacetamido]-3-[(1H-1,2,4-triazol-5-yl)thiomethyl]-3-cephem-4-carboxylic acid, 7β-[D-2-(6,7-Dihydroxychromone-3-carboxamido)-2-phenylacetamido]-3-[(1-methylimidazol-2-yl)thiomethyl]-3-cephem-4-carboxylic acid, 7β-[D-2-(6,7-dihydroxychromone-3-carboxamido)-2-phenylacetamido]-3-(2-pyrimidinylthiomethyl)-3-cephem-4-carboxylic acid, 7β-[D-2-(6,7-Dihydroxychromone-3-carboxamido)-2-phenylacetamido]-3-(2-benzothiazolylthiomethyl)-3-cephem-4-carboxylic acid, 7β-[D-2-(6,7-Dihydroxychromone-3-carboxamido)-2-(4-hydroxyphenyl)acetamido]-3-[(1-methyltetrazol-5-yl) thiomethyl]-3-cephem-4-carboxylic acid, 7β-[D-2-(6,7-Dihydroxychromone-3-carboxamido)-2-(4-hydroxyphenyl)acetamido]-3-[(5-methyl-1,3,4-thiadiazol-2-yl)thiomethyl]-3-cephem-4-carboxylic acid, 7β-[D-2-(6,7-Dihydroxychromone-3-carboxamido)-2-(4-hydroxyphenyl)acetamido]-3-[[1-(2-dimethylaminoethyl)tetrazol-5-yl]thiomethyl]-3-cephem-4-carboxylic acid, 7β-[D-2-(6,7-Diacetoxychromone-3-carboxamido)-2-phenylacetamido]-3-[(1-methyltetrazol-5-yl)thiomethyl]-3-cephem-4-carboxylic acid, 7β-[D-2-(6,7-Diacetoxychromone-3-carboxamido)-2-phenylacetamido]-3-[(5-methyl-1,3,4-thiadiazol-2-yl)thiomethyl]-3-cephem-4-carboxylic acid, 7β-[D-2-(6,7-Diacetoxychromone-3-carboxamido)-2-phenylacetamido]-3-[[1-(2-dimethylminoethyl)tetrazol-5-yl]thiomethyl]-3-cephem-4-carboxylic acid, 7β-[D-2-(6,7-Diacetoxychromone-3-carboxamido)-2-(4-hydroxyphenyl)acetamido]-3-[(1-methyltetrazol-5-yl)-thiomethyl]-3-cephem-4-carboxylic acid, 7β-[D-2-(6,7-Diacetoxychromone-3-carboxamido)-2-(4-hydroxyphenyl)acetamido]-3-[(5-methyl-1,3,4-thiadiazol-2-yl)thiomethyl]-3-cephem-4-carboxylic acid, 7β-[D-2-(6,7-Diacetoxychromone-3-carboxamido)-2-(4-hydroxyphenyl)acetamido]-3-[[1-(2-dimethylamino ethyl) tetrazol-5-yl]thiomethyl]-3-cephem-4-carboxylic acid, 7β-[D-2-(7,8-Dihydroxychromone-3-carboxamido)-2-phenylacetamido]-3-[(5-methyl-1,3,4-thiadiazol-2-yl)thiomethyl]-3-cephem-4-carboxylic acid, 7β-[D-2-(7,8-Dihydroxychromone-3-carboxamido)-2-phenylacetamido]-3-[(1-methyltetrazol-5-yl)thiomethyl]-3-cephem-4-carboxylic acid, 7β-[D-2(7,8-Dihydroxychromone-3-carboxamido)-2-(4-hydroxyphenyl)acetamido]-3-[(5-methyl-1,3,4-thiadiazol-2-yl) thiomethyl]-3-cephem-4-carboxylic acid, 7β-[D-2-(7,8-Dihydroxychromone-3-carboxamido)-2-(4-hydroxyphenyl)acetamido]-3-[(1-methyltetrazol-5-yl)thiomethyl]-3-cephem-4-carboxylic acid, 7β-[D-2-(7,8-Diacetoxychromone-3-carboxamido)-2-phenylacetamido]-3-[(5-methyl-1,3,4-thiadiazol-2-yl)thiomethyl]-3-cephem-4-carboxylic acid, 7β-[D-2-(7,8-Diacetoxychromone-3-carboxamido)-2-phenylacetamido]-3-[(1-methyltetrazol-5-yl)thiomethyl]-3-cephem-4-carboxylic acid, 7β-[D-2-(7,8-Diacetoxychromone-3-carboxamido)-2-(4-hydroxyphenyl)acetamido]-3-[(5-methyl-1,3,4-thiadiazol-2-yl)thiomethyl]-3-cephem-4-carboxylic acid, 7β-[D-2-(7,8-Diacetoxychromone-3-carboxamido)-2-(4-hydroxphenyl)acetamido]-3-[(1-methyltetrazol-5-yl)thiomethyl]-3-cephem-4-carboxylic acid, 7β-[D-2-(7-Hydroxychromone-3-carboxamido)-2-(4-hydroxyphenyl)acetamido]-3-[(1-methyltetrazol-5-yl)thiomethyl]-3-cephem-4-carboxylic acid, 7β-[D-2-(6-Acetoxychromone-3-carboxamido)-2-(4-hydroxyphenyl)acetamido]-3-[(1-methyltetrazol-5-yl)thiomethyl]-3-cephem-4-carboxylic acid, 7β-[D-2-(Chromone-3-carboxamido)-2-(4-hydroxyphenyl) acetamido]-3-[(1-methyltetrazol-5-yl)thiomethyl]-3-cephem-4-carboxylic acid, 7β-[D-2(6,7,8-Trihydroxychromone-3-carboxamido)-2-(4-hydroxphenyl)acetamido]-3-[(1-methyltetrazol-5-yl)thiomethyl]-3-cephem-4-carboxylic acid, 7β-[D-2-(6,7-Dihydroxychromone-3-carboxamido)-2-(4-hydroxyphenyl)acetamido]-3-[(1,3,4-thiadiazol-2-yl)thiomethyl]-3-cephem-4-carboxylic acid, 7β-[D-2-(6,7-Dihydroxychromone-3-carboxamido)-2-(4-hydroxyphenyl)acetamido]-3-[(1-ethyltetrazol-5-yl)thiomethyl-3-cephem-4-carboxylic acid, 7β-[D-2-(6,7-Dihydroxychromone-3-carboxamido)-2-(4-hydroxyphenyl)acetamido]-3-[(4H-1,2,4-triazol-3-yl)thiomethyl]-3-cephem-4-carboxylic acid, 7β-[D-2-(6,7-Dihydroxychromone-3-carboxamido)-2-(4-hydroxyphenyl)acetamido]-3-[(1-carboxymethyltetrazol-5-yl) thiomethyl]-3-cephem-4-carboxylic acid, 7β-[D-2-(6,7-Dihydroxychromone-3-carboxamido)-2-(4-hydroxyphenyl)acetamido]-3-(2-pyridylthiomethyl)-3-cephem-4-carboxylic acid, 7β-[D-2-(6,7-Dihydroxychromone-3-carboxamido)-2-(4-hydroxyphenyl)acetamido]-3-[2-(pyridyl-1-oxido)-thiomethyl]-3-cephem-4-carboxylic acid, 7β-[D-2-(6,7-Dihydroxychromone-3-carboxamido)-2-(4-hydroxyphenyl)acetamido]-3-(2-pyrimidinylthiomethyl)-3-cephem-4-carboxylic acid, 7β-[D-2-(6,7-Dihydroxychromone-3-carboxamido)-2-(4-hydroxyphenyl)acetamido]-3-[(5-methyl-1,3,4- oxadiazol-2-yl) thiomethyl]-3-cephem-4-carboxylic acid,

7β-[D-2-(6,7,8-Triacetoxychromone-3-carboxamido)-2-(4-hydroxyphenyl)acetamido]-3-[(1-methyltetrazol-5-yl)thiomethyl]-3-cephem-4-carboxylic acid, 7β-[D-2-(6,7,8-Trihydroxychromone-3-carboxamido)-2-(4-hydroxyphenyl)acetamido]-3-[(1-carboxymethyltetrazol-5-yl) thiomethyl]-3-cephem-4-carboxylic acid; and 7β-[D-2-(6,7,8-Triacetoxychromone-3-carboxamido)-2-(4-hydroxyphenyl)acetamido]-3-[(1-carboxymethyltetrazol-5-yl)-thiomethyl]-3-cephem-4-carboxylic acid.

The compounds of this invention exhibit excellent antibacterial activity, and are effective not only against the Gram-positive bacteria, but also against the Gram-negative bacteria. Particularly, the compounds of this invention are characterized in that they are effective against those bacteria such as *Pseudomonas aeruginosa, Serritia marcescens, Proteus morganii,* and the like that cause hardly curable infections.

The compounds of this invention exhibit low toxicity in the toxicity test. The acute toxicity values [LD$_{50}$ (mouse, oral)] for the following compounds, for example, were over 5 g/kg:

Sodium salt of 7β-[D-2-(6,7-dihydroxychromone-3-carboxamido)-2-phenylacetamido]-3-[(1-methyltetrazol-5-yl)-thiomethyl]-3-cephem-4-carboxylic acid;

Sodium salt of 7β-[D-2-(6,7-dihydroxychromone-3-carboxamido)-2-(4-hydroxyphenyl)acetamido]-3-[(5-methyl-1,3,4-thiadiazol-2-yl)thiomethyl]-3-cephem-4-carboxylic acid; and Sodium salt of 7β-[D-2-(6,7-diacetoxychromone-3-carboxamido)-2-phenylacetamido]-3-[(1-methyltetrazol-5-yl)thiomethyl]-3-cephem-4-carboxylic acid.

The dose of the compound of this invention, when used as an antibacterial drug, may range generally from 2 to 300 mg/kg/day, preferably from 10 to 100 mg/kg/day. This medicine can be administered orally in the form of powder, granule, tablet, capsule, syrup, and the like, or parenterally in the form of injection, suppository, and the like.

These preparations can be provided by conventional processes. The preparations of powder, granule, tablet and capsule can be provided using appropriately excipients such as lactose, starch, white sugar, glucose, crystallized cellulose, and the like; disintegrants, such as, starch, calcium ssalt or carboxymethylcellulose, calcium carbonate, dextrine, and the like; binders such as polyvinyl alcohol, ethylcellulose, gum arabic, tragacanth, hydroxypropylcellulose; and lubricants such as calcium stearate, magnesium stearate, talc, and the like.

The preparations of syrup can be provided using appropriate sweetenings such as white sugar, sorbitol, glucose, fructose, and the like; dispersants and thickeners such as gum arabic, tragacanth, sodium salt of carboxymethylcellulose, methylcellulose, sodium arginate, and the like.

The preparations for injection can be provided using isotonic agents such as glucose, sodium chloride, sorbitol, and the like, and if required, suspending agents, surfactants, pH controlling agents, and the like. Alternatively, the preparation for injection may be in the form of powder which can be dissolved prior to administration.

The suppository can be provided using a basis such as cacao butter, polyethylene glycol, Witepsol (trade mark, Dynamite-Nobel-AG), and the like and, if required, a surfactant.

The following experiments and examples illustrate this invention, but are not to be construed as limiting the scope thereof.

EXPERIMENT I

Preparation of chromone-3-carboxylic acids which are the intermediates of the compounds of this invention.

(A) 6,7-Diacetoxychromone-3-carboxylic acid 6,7-Diacetoxychromone-3-carboxaldehyde (17.8 g) were dissolved in 1 litre of acetone. To this solution were added with stirring Jones reagent (32.8 ml) which had been previously prepared by dissolving chromic acid (133.6 g) in concentrated sulfuric acid (115 ml) diluted with water to a volume of 500 ml.

The reaction mixture was concentrated to 100 ml, and poured into water (900 ml). The precipitates (6.5 g) were collected by filtration, and recrystallized from ethyl acetate to obtain the desired compound (5.9 g).

(B) 6,7-Dihydroxychromone-3-carboxylic acid

To 6,7-diacetoxychromone-3-carboxylic acid (15.3 g) produced in (A) were added acetic acid (300 ml) and concentrated hydrochloric acid (100 ml), and the mixture was stirred for 20 minutes at about 70° C., then cooled. The precipitates were collected by filtration, and recrystallized from dimethylformamide-water to obtain the desired compound (8.9 g).

Other compounds containing no hydroxy group were prepared by the process according to (A), while the compounds containing hydroxy were prepared by the process according to (B). The properties of the resulting compounds were shown in Table 1.

TABLE 1

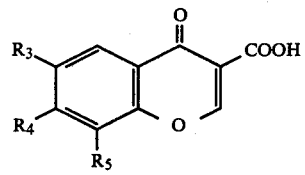

(III)

| No. | R$_3$ (III) | R$_4$ | R$_5$ | Infrared Absorption Spectrum (cm$^{-1}$, nujol) | Molecular Formula Melting Point (°C.) | Elemental Analysis (%) Calculated: Found: C | H |
|---|---|---|---|---|---|---|---|
| 1 | HO— | HO | H | 3370, 3300, 1730, 1635, 1620 | C$_{10}$H$_6$O$_6$ >300 | 54.06 54.05 | 2.72 2.60 |
| 2 | CH$_3$COO— | CH$_3$COO— | H | 1780, 1760, 1730, 1620 | C$_{14}$H$_{10}$O$_8$ 186–188 | 54.91 54.95 | 3.29 3.08 |

TABLE 1-continued (III)

[Structure: chromone with R3, R4, R5 substituents and COOH at 3-position]

| No. | R3 (III) | R4 | R5 | Infrared Absorption Spectrum (cm⁻¹, nujol) | Molecular Formula Melting Point (°C.) | Elemental Analysis (%) Calculated: Found: C | H |
|---|---|---|---|---|---|---|---|
| 3 | H | HO— | HO— | 3380, 3275, 1725, 1620 | $C_{10}H_6O_6$ 265-270* | 54.06 53.65 | 2.72 2.53 |
| 4 | H | CH3COO— | CH3COO— | 1780, 1760, 1740, 1625 | $C_{14}H_{10}O_8$ 178-179 | 54.91 54.90 | 3.29 3.25 |
| 5 | H | HO— | H | 1720, 1625 | $C_{10}H_6O_5$ 271-273* | 58.26 58.21 | 2.93 2.80 |
| 6 | CH3COO— | H | H | 1770, 1760, 1625 | $C_{12}H_8O_6$ 169-170 | 58.07 57.95 | 3.25 3.20 |
| 7 | H | H | H | 1755, 1620-1650 | $C_{10}H_6O_4$ 200-201 | 63.16 63.22 | 3.18 2.96 |
| 8 | HO— | HO— | HO— | 1720, 1630 | $C_{10}H_6O_7$ >280 | 50.43 50.22 | 2.54 2.61 |
| 9 | CH3COO— | CH3COO— | CH3COO— | 1780, 1690 1650, 1615 | $C_{16}H_{12}O_{10}$ 192-195 | 52.76 52.65 | 3.32 3.30 |

*: With decomposition

EXAMPLE 1

7β-[D-2-(6,7-Dihydroxychromone-3-carboxamido)-2-phenyl-acetamido]-3-[(1-methyltetrazol-5-yl)thiomethyl]-3-cephem-4-carboxylic acid and its sodium salt (a) 6,7-Dihydroxychromone-3-carbonyl chloride A mixture of 6,7-dihydroxychromone-3-carboxylic acid (888 mg, 4 mmol) and thionyl chloride (25 ml) was refluxed for one hour and the thionyl chloride was evaporated. After the addition of benzene, the mixture was evaporated again to dryness and the residue was triturated with dichloromethane to give the desired compound (719 mg).

Infrared absorption spectrum (cm⁻¹, nujol): 1780, 1765, 1645, 1625

(b)
7β-[D-2-(6,7-Dihydroxychromone-3-carboxamido)-2-phenylacetamido]-3-[(1-methyltetrazol-5-yl)thiomethyl]-3-cephem-4-carboxylic acid N,O-Bis(trimethylsilyl)acetamide (420 μl) was added to a stirred suspension of 7β-(D-2-amino-2-phenylacetamido)-3-[(1-methyltetrazol-5-yl)thiomethyl]-3-cephem-4-carboxylic acid (146 mg, 0.316 mmol) in ethyl acetate (5.5 ml) at 0° C. and the mixture was stirred for 20 minutes at 0° C. After the addition of the acid chloride (67.3 mg, 0.283 mmol) described in (a), the mixture was stirred for 4 hours at room temperature. The reaction mixture was diluted with ethyl acetate (150 ml), washed with water and then with saturated brine, dried (MgSO4), and the solvent was removed. Trituration of the residue with ethyl acetate afforded the desired product (88 mg, 44%).

Melting point: 225°–245° C. (decomposition)

| Elemental analysis for $C_{28}H_{23}N_7O_9S_2$ | | | |
|---|---|---|---|
| | C | H | N |
| Calculated (%): | 50.52 | 3.48 | 14.73 |
| Found (%): | 47.54 | 3.37 | 12.70 |

Infrared absorption spectrum (cm⁻¹, nujol): 1780, 1710, 1665, 1630

NMR spectrum (δ, DMSO-d6): 3.52 (1H, d, J=17 Hz), 3.70 (1H, d, J=17 Hz), 3.94 (3H, s), 4.20 (1H, d, J=13 Hz), 4.37 (1H, d, J=13 Hz), 5.02 (1H, d, J=5 Hz), 5.74 (1H, dd, J=8 Hz, 5 Hz), 5.84 (1H, d, J=8 Hz), 7.00 (1H, s), 7.2–7.6 (5H, m), 7.44 (1H, s), 8.87 (1H, s), 9.52 (1H, d, J=8 Hz), 10.40 (1H, d, J=8 Hz).

(c) Sodium salt of the compound described in (b)

The compound (55 mg, 0.083 mmol) described in (b) was dissolved in a mixture of acetone (2 ml) and dimethylformamide (1 ml), to which was added 0.5 M solution of sodium 2-ethylhexanoate in ethyl acetate (0.16 ml) followed by ethyl acetate-ethyl ether (1:1, 10 ml). The precipitates were collected by filtration, washed with ethyl acetate-ethyl ether (1:1) and dried to give the desired compound (53 mg, 94%).

Melting point: about 230° C. (decomposition)

| Elemental analysis for $C_{28}H_{22}N_7NaO_9S_2$ | | | |
|---|---|---|---|
| | C | H | N |
| Calculated (%): | 48.90 | 3.22 | 14.26 |
| Found (%): | 44.45 | 3.35 | 12.60 |

Infrared absorption spectrum (cm⁻¹, nujol): 1765, 1660, 1610

NMR spectrum (δ, DMSO-d6): 3.30 (1H, d, J=18 Hz), 3.43 (1H, d, J=18 Hz), 3.90 (3H, s), 4.19 (1H, d, J=12 Hz), 4.40 (1H, d, J=12 Hz), 4.88 (1H, d, J=5 Hz), 5.56 (1H, dd, J=8 Hz, 5 Hz), 5.83 (1H, d, J=8 Hz), 6.88 (1H, s), 7.32 (1H, s), 7.2–7.6 (5H, m), 8.75 (1H, s), 9.40 (1H, d, J=8 Hz), 10.48 (1H, d, J=8 Hz)

EXAMPLE 2

7β-[D-2-(6,7-Dihydroxychromone-3-carboxamido)-2-phenyl-acetamido]-3-[(5-methyl-1,3,4-thiadiazol-2-yl)thiomethyl]-3-cephem-4-carboxylic acid and its sodium salt

(a)

7β-[D-2-(6,7-Dihydroxychromone-3-carboxamido)-2-phenylacetamido]-3-[(5-methyl-1,3,4-thiadiazol-2-yl)thiomethyl]-3-cephem-4-carboxylic acid In accordance with the process described in Example 1-b), 7β-(D-2-amino-2-phenylacetamido)-3-[(5-methyl-1,3,4-thiadiazol-2-yl)thiomethyl]-3-cephem-4-carboxylic acid (266 mg, 0.557 mmol) was treated with the acid chloride (120 mg, 0.5 mmol) described in Example 1-a) to obtain the desired compound (65 mg, 44%).

Melting point: 215°–235° C. (decomposition)

| Elemental analysis for $C_{29}H_{23}N_5O_9S_3$ | | | |
|---|---|---|---|
| | C | H | N |
| Calculated (%): | 51.09 | 3.40 | 10.27 |
| Found (%): | 49.14 | 3.14 | 8.54 |

Infrared absorption spectrum (cm$^{-1}$, nujol): 1780, 1725, 1660, 1610–1630

NMR spectrum (δ, DMSO-d$_6$): 2.69 (3H, s), 3.48 (1H, d, J=18 Hz), 3.71 (1H, d, J=18 Hz), 4.17 (1H, d, J=13 Hz), 4.52 (1H, d, J=13 Hz), 5.04 (1H, d, J=5 Hz), 5.79 (1H, dd, J=8 Hz, 5 Hz), 5.85 (1H, d, J=8 Hz), 7.00 (1H, s), 7.2–7.6 (5H, m), 7.44 (1H, s), 8.88 (1H, s), 9.52 (1H, d, J=8 Hz), 10.40 (1H, d, J=8 Hz)

(b) Sodium salt of the compound described in (a)

In accordance with the process described in Example 1-c), the desired compound (43 mg, 99%) was obtained from the compound (42 mg, 0.0616 mmol) described in (a).

Melting point: about 250° C. (decomposition)

| Elemental analysis: for $C_{29}H_{22}N_5NaO_9S_3$ | | | |
|---|---|---|---|
| | C | N | H |
| Calculated (%): | 49.49 | 3.15 | 9.95 |
| Found (%): | 47.11 | 3.61 | 8.80 |

Infrared absorption spectrum (cm$^{-1}$, nujol): 1760, 1660, 1610

NMR spectrum (δ, DMSO-d$_6$): 2.65 (3H, s), 3.27 (1H, d, J=18 Hz), 3.53 (1H, d, J=18 Hz), 4.30 (1H, d, J=12 Hz), 4.50 (1H, d, J=12 Hz), 4.89 (1H, d, J=5 Hz), 5.56 (1H, dd, J=8 Hz, 5 Hz), 5.84 (1H, d, J=8 Hz), 6.83 (1H, s), 7.30 (1H, s), 7.2–7.6 (5H, m), 8.76 (1H, s), 9.40 (1H, d, J=8 Hz), 10.51 (1H, d, J=8 Hz)

EXAMPLE 3

7β-[D-2-(6,7-Dihydroxychromone-3-carboxamido)-2-(4-hydroxyphenyl)acetamido]-3-[(1-methyltetrazol-5-yl)-thiomethyl]-3-cephem-4-carboxylic acid and its sodium salt

(a)

7β-[D-2-(6,7-Dihydroxychromone-3-carboxamido)-2-(4-hydroxyphenyl)acetamido]-3-[(1-methyltetrazol-5-yl)thiomethyl]-3-cephem-4-carboxylic acid N,O-Bis(trimethylsilyl)acetamido (455 μl) was added to a stirred suspension of 7β-[D-2-amino-2-(4-hydroxyphenyl) acetamido]-3-[(1-methyltetrazol-5-yl)thiomethyl]-3-cephem-4-carboxylic acid (140 mg, 0.293 mmol) in ethyl acetate (6 ml) at 0° C., and the stirring was continued for 20 minutes at 0° C. After the addition of the acid chloride (67.3 mg, 0.263 mmol) described in Example 1-a), the mixture was stirred for 2 hours at 0° C. The reaction mixture was diluted with ethyl acetate (150 ml), washed successively with 0.5 N hydrochloric acid (20 ml×2), water (20 ml×4) and saturated brine (20 ml×2) and dried (MgSO$_4$) and the solvent was removed. Acetone was added to the residue and the mixture was allowed to stand overnight. The solvent was removed and the residue was triturated with ethyl ether to give the desired compound (123 mg, 69%).

Melting point: about 195°–220° C. (decomposition)

| Elemental analysis: for $C_{28}H_{23}N_7O_{10}S_2$ | | | |
|---|---|---|---|
| | C | H | N |
| Calculated (%): | 49.33 | 3.40 | 14.39 |
| Found (%): | 48.41 | 4.11 | 12.37 |

Infrared absorption spectrum (cm$^{-1}$, nujol): 1780, 1725, 1660, 1610

NMR spectrum (δ, DMSO-d$_6$): 3.62 (2H, br), 3.93 (3H, s), 4.21 (1H, d, J=14 Hz), 4.37 (1H, d, J=14 Hz), 5.02 (1H, d, J=5 Hz), 5.64–5.84 (2H, m), 6.73 (2H, d, J=8.5 Hz), 6.99 (1H, s), 7.25 (2H, d, J=8.5 Hz), 7.43 (1H, s), 8.86 (1H, s), 9.37 (1H, d, J=8 Hz), 9.43 (1H, br.s), 10.1 (1H, br), 10.25 (1H, d, J=8 Hz), 10.7 (1H, br).

(b) Sodium salt of the compound described in (a)

The compound (70 mg, 0.103 mmol) described in (a) was dissolved in a mixture of acetone (3 ml) and dimethylformamide (2 ml). To this solution was added a 0.5 M solution of sodium 2-ethylhexanoate in ethyl acetate (0.21 ml) followed by ethyl acetate-ethyl ether (1:1, 10 ml). The precipitates were collected by filtration, washed with ethyl acetate-ether (1:1) and dried to give the desired compound (57 mg, 79%).

Melting point: about 200° C. (decomposition)

| Elemental analysis: for $C_{28}H_{22}N_7NaO_{10}S_2$ | | | |
|---|---|---|---|
| | C | H | N |
| Calculated (%): | 47.79 | 3.15 | 13.94 |
| Found (%): | 44.52 | 3.60 | 12.62 |

Infrared absorption spectrum (cm$^{-1}$, nujol): 1760, 1660, 1605

NMR spectrum (δ, DMSO-d$_6$): 3.34 (1H, d, J=18 Hz), 3.57 (1H, d, J=18 Hz), 3.92 (3H, s), 4.23 (1H, d, J=12 Hz), 4.42 (1H, d, J=12 Hz), 4.91 (1H, d, J=5 Hz), 5.59 (1H, dd, J=8 Hz, 5 Hz), 5.72 (1H, d, J=8 Hz), 6.73 (2H, d, J=8.5 Hz), 6.97 (1H, s) 7.26 (2H, d, J=8.5 Hz), 7.36 (1H, s), 8.80 (1H, s), 9.32 (1H, d, J=8 Hz), 10.36 (1H, d, J=8 Hz)

EXAMPLE 4

7β-[D-2-(6,7-Dihydroxychromone-3-carboxamido)-2-(4-hydroxyphenyl)acetamido[-3-[(5-methyl-1,3,4-thiadiazol-2-yl)thiomethyl]-3-cephem-4-carboxylic acid and its sodium salt (a) 7β-[D-2-(6,7-Dihydroxychromone-3-carboxamido)-2-(4-hydroxyphenyl)acetamido]-3-[(5-methyl-1,3,4-thiadiazol-2-yl)thiomethyl]-3-cephem-4-carboxylic acid In accordance with the process described in Example 1-(b), 7β-[D-2-amino-2-(4-hydroxyphenyl)acetamido]-3-[(5-methyl-1,3,4-thiadiazol-2-yl)thiomethyl]-3-cephem-4-carboxylic acid (274 mg, 0.555 mmol) was treated with the acid chloride (120 mg, 0.5 mmol) described in Example 1-a) to give the desired compound (143 mg, 41%).

Melting point: about 228°–260° C. (decomposition)

Elemental analysis: for $C_{29}H_{23}N_5O_{10}S_3$

|  | C | H | N |
|---|---|---|---|
| Calculated (%): | 49.92 | 3.32 | 10.04 |
| Found (%): | 47.35 | 2.98 | 8.84 |

Infrared absorption spectrum (cm$^{-1}$, nujol): 1775, 1730, 1710, 1660, 1615

NMR spectrum (δ, DMSO-d$_6$): 2.70 (3H, s), 3.49 (1H, d, J=18 Hz), 3.71 (1H, d, J=18 Hz), 4.19 (1H, d, J=13 Hz), 4.51 (1H, d, J=13 Hz), 5.04 (1H, d, J=5 Hz), 5.64–5.84 (2H, m), 6.73 (2H, d, J=8.5 Hz), 7.00 (1H, s), 7.26 (2H, d, J=8.5 Hz), 7.43 (1H, s), 8.87 (1H, s), 9.38 (1H, d, J=8 Hz), 10.24 (1H, d, J=8 Hz)

(b) Sodium salt of the compound described in (a)

In accordance with the process described in Example 1-c), the desired compound (114 mg, 100%) was obtained from the compound (110 mg, 0.158 mmol) described in (a).

Melting point: about 230° C. (decomposition)

Elemental analysis: for $C_{29}H_{22}N_5NaO_{10}S_3$

|  | C | H | N |
|---|---|---|---|
| Calculated (%): | 48.39 | 3.08 | 9.73 |
| Found (%): | 45.59 | 3.45 | 9.48 |

Infrared absorption spectrum (cm$^{-1}$, nujol): 1765, 1660, 1615

NMR spectrum (δ, DMSO-d$_6$): 2.65 (3H, s), 3.30 (1H, d, J=18 Hz), 3.55 (1H, d, J=18 Hz), 4.30 (1H, d, J=12 Hz), 4.51 (1H, d, J=12 Hz), 4.90 (1H, d, J=5 Hz), 5.56 (1H, dd, J=8 Hz, 5 Hz), 5.61 (1H, d, J=8 Hz), 6.71 (2H, d, J=8.5 Hz), 6.89 (1H, s), 7.23 (2H, d, J=8.5 Hz), 7.31 (1H, s), 8.75 (1H, s), 9.28 (1H, d, J=8 Hz), 10.35 (1H, d, J=8 Hz)

EXAMPLE 5

7β-[D-2-(6,7-Diacetoxychromone-3-carboxamido)-2-phenyl-acetamido]-3-[(1-methyltetrazol-5-yl)thiomethyl]-3-cephem-4-carboxylic acid and its sodium salt (a) 6,7-Diacetoxychromone-3-carbonyl chloride A mixture of 6,7-diacetoxychromone-3-carboxylic acid (18.4 g, 60 mmol), benzene (450 ml), thionyl chloride (8.6 g, 72 mmol) and dimethylformamide (3 ml) was refluxed for one hour, and cooled to room temperature. After the addition of n-hexane (300 ml), the resulting precipitate was collected to give the desired compound (17.6 g).

Infrared absorption spectrum (cm$^{-1}$, nujol): 1780, 1755, 1660, 1625

(b) 7β-[D-2-(6,7-Diacetoxychromone-3-carboxamido)-2-phenylacetamido]-3-[(1-methyltetrazol-5-yl)thiomethyl]-3-cephem-4-carboxylic acid To a stirred suspension of 7β-(D-2-amino-2-phenylacetamido)-3-[(1-methyltetrazol-5-yl)thiomethyl]-3-cephem-4-carboxylic acid (516 mg, 1.12 mmol) in ethyl acetate (5 ml) at 0° C. was added dropwise a 1 M solution (5 ml) of N,O-bis (trimethylsilyl)-acetamide in dichloromethane. The solution was stirred for 20 minutes at 0° C., to which was added a solution of the acid chloride (325 mg, 1 mmol) described in (a) in dichloromethane (5 ml). After stirring for 4 hours at 0° C., the mixture was diluted with ethyl acetate (300 ml), washed with water (20 ml), 0.5 N hydrochloric acid (20 ml×2), water (20 ml×2) and saturated brine (20 ml×2), dried (MgSO$_4$) and the solvent was evaporated. The residue was triturated with ethyl ether to give the desired compound (575 mg, 77%).

Melting point: about 200°–240° C. (decomposition)

Elemental analysis: for $C_{32}H_{27}N_7O_{11}S_2$

|  | C | H | N |
|---|---|---|---|
| Calculated (%): | 51.26 | 3.63 | 13.08 |
| Found (%): | 50.99 | 3.83 | 12.95 |

Infrared absorption spectrum (cm$^{-1}$, nujol): 1780, 1760, 1662, 1615

NMR spectrum (δ, DMSO-d$_6$): 2.35 (3H, s), 2.37 (3H, s), 3.53 (1H, d, J=18 Hz, 3.71 (1H, d, J=18 Hz), 3.94 (3H, s), 4.22 (1H, d, J=13 Hz), 4.37 (1H, d, J=13 Hz), 5.03 (1H, d, J=5 Hz), 5.77 (1H, dd, J=8 Hz, 5 Hz), 5.84 (1H, d, J=8 Hz), 7.2–7.6 (5H, m), 7.88 (1H, s), 8.08 (1H, s), 9.04 (1H, s), 9.76 (1H, d, J=8 Hz), 10.13 (1H, d, J=8 Hz), 10.13 (1H, d, J=8 Hz)

(c) Sodium salt of the compound (b)

According to the process described in Example 1-c), the desired compound (355 mg, 66%) was obtained from the compound (525 mg, 0.7 mmol) described in (b).

Melting point: about 205° C. (decomposition)

Elemental analysis: for $C_{32}H_{26}N_7NaO_{11}S_2$

|  | C | H | N |
|---|---|---|---|
| Calculated (%): | 49.80 | 3.40 | 12.71 |
| Found (%): | 46.27 | 3.45 | 10.44 |

Infrared absorption spectrum (cm$^{-1}$, nujol): 1770, 1670, 1620

EXAMPLE 6

7β-[D-2-(6,7-Diacetoxychromone-3-carboxamido)-2-phenylacetamido]-3-[(5-methyl-1,3-4-thiadiazol-2-yl)thiomethyl]-3-cephem-4-carboxylic acid and its sodium salt (a)

7β-[D-2-(6,7-Diacetoxychromone-3-carboxamido)-2-phenylacetamido]-3-[(5-methyl-1,3,4-thiadiazol-2-yl)thiomethyl]-3-cephem-4-carboxylic acid To a stirred suspension of 7β-(D-2-amino-2-phenylacetamido)-3-[(5-methyl-1,3,4-thiadiazol-2-yl)thiomethyl]-3-cephem-4-carboxylic acid (239 mg, 0.5 mmol) in ethyl acetate (5.5 ml) was added dropwise a 1 M solution (2.5 ml) of N,O-bis(trimethylsilyl)acetamide in dichloromethane. The solution was stirred for 20 minutes at 0° C., to which was added the acid chloride (243 mg, 0.75 mmol) described in Example 5-a). After stirring for 4 hours at 0° C., the mixture was diluted with ethyl acetate (150 ml), washed with water (20 ml), 0.5 N hydrochloric acid (20 ml×2), water (20 ml×2) and saturated brine (20 ml×2), the solvent was dried (MgSO$_4$) and evaporated. The residue was triturated with ethyl ether to give the desired compound (253 mg, 66%).

Melting point: 166°-178° C. (decomposition)

| Elemental analysis: for C$_{33}$H$_{27}$N$_5$O$_{11}$S$_3$ | | | |
|---|---|---|---|
| | C | H | N |
| Calculated (%): | 51.76 | 3.55 | 9.15 |
| Found (%): | 50.34 | 3.40 | 7.75 |

Infrared absorption spectrum (cm$^{-1}$, nujol): 1785, 1770, 1725, 1680, 1660, 1615

NMR spectrum (δ, DMSO-d$_6$): 2.37 (6H, s), 2.70 (3H, s), 3.48 (1H, d, J=18 Hz), 3.71 (1H, d, J=18 Hz), 4.17 (1H, d, J=13 Hz), 4.53 (1H, d, J=13 Hz), 5.04 (1H, d, J=5 Hz), 5.77 (1H, d, J=5 Hz), 5.88 (1H, d, J=8 Hz), 7.2–7.6 (5H, m), 7.89 (1H, s), 9.05 (1H, s), 9.55 (1H, d, J=8 Hz), 10.13 (1H, d, J=8 Hz)

(b) Sodium salt of the compound described in (a)

The compound (208 mg, 0.272 mmol) described in (a) was dissolved in a mixture of acetone (3 ml) and ethyl acetate (3 ml). To this solution was added a 0.5 M solution (0.55 ml) of sodium 2-ethylhexanoate in ethyl acetate followed by ethyl acetate-ether (1:1, 10 ml). The precipitate was collected, washed with ethyl acetate-ethyl ether (1:1) and dried to give the desired compound (168 mg, 78%).

Melting point: 190°-220° C. (decomposition)

| Elemental analysis: for C$_{33}$H$_{26}$N$_5$NaO$_{11}$S$_3$ | | | |
|---|---|---|---|
| | C | H | N |
| Calculated (%): | 50.31 | 3.33 | 8.89 |
| Found (%): | 48.92 | 3.62 | 8.68 |

Infrared absorption spectrum (cm$^{-1}$, nujol): 1780, 1760, 1675, 1665, 1600–1630

NMR spectrum (δ, DMSO-d$_6$): 2.34 (3H, s), 2.35 (3H, s), 2.66 (3H, s), 3.26 (1H, d, J=18 Hz), 3.52 (1H, d, J=18 Hz), 4.30 (1H, d, J=12 Hz), 4.50 (1H, d, J=12 Hz), 4.90 (1H, d, J=5 Hz), 5.64 (1H, dd, J=8 Hz, 5 Hz), 5.87 (1H, d, J=8 Hz), 7.2–7.56 (5H, m), 7.85 (1H, s), 8.05 (1H, s), 9.01 (1H, s), 9.43 (1H, d, H=8 Hz), 10.10 (1H, d, J=8 Hz)

EXAMPLE 7

7β-[D-2-(6,7-Diacetoxychromone-3-carboxamido)-2-(4-hydroxyphenyl)acetamido]-3-[(1-methyltetrazol-5-yl)thiomethyl]-3-cephem-4-carboxylic acid and its sodium salt (a)

7β-[D-2-(6,7-Diacetoxychromone-3-carboxamido)-2-(4-hydroxyphenyl)acetamido]-3-[(1-methyltetrazol-5-yl)thiomethyl]-3-cephem-4-carboxylic acid Accroding to the process described in Example 3-a), 7β-[D-2-amino-2-(4-hydroxyphenyl)acetamido]-3-[(1-methyltetrazol-5-yl)thiomethyl]-3-cephem-4-carboxylic acid (140 mg, 0.293 mmol) was treated with the acid chloride (85.2 mg, 0.263 mmol) described in Example 5-a) to give the desired compound (184 mg, 91%).

Melting point: about 215°-240° C. (decomposition)

| Elemental analysis: for C$_{32}$H$_{27}$N$_7$O$_{12}$S$_2$ | | | |
|---|---|---|---|
| | C | H | N |
| Calculated (%): | 50.19 | 3.55 | 12.81 |
| Found (%): | 49.92 | 3.83 | 11.88 |

Infrared absorption spectrum (cm$^{-1}$, nujol): 1760–1800, 1720, 1660–1680, 1615

NMR spectrum (δ, DMSO-d$_6$): 2.34 (3H, s), 2.35 (3H, s), 3.60 (2H, br), 3.92 (3H, s) 4.20 (1H, d, J=14 Hz), 4.36 L (1H, d, J=14 Hz), 5.02 (1H, d, J=5 Hz), 5.64–5.84 (2H, m), 6.73 (2H, d, J=8.5 Hz), 7.26 (2H, d, J=8.5 Hz), 7.87 (1H, s), 8.05 (1H, s), 9.03 (1H, s), 9.40 (1H, d, J=8 Hz), 9.45 (1H, br.s), 9.99 (1H, d, J=8 Hz)

(b) Sodium salt of the compound described in (a)

In accordance with the process described in Example 3-b), the desired compound (95 mg, 92%) was obtained from the compound (100 mg, 0.13 mmol) described in (a).

Melting point: about 210° C. (decomposition)

| Elemental analysis: for C$_{32}$H$_{26}$N$_7$NaO$_{12}$S$_2$ | | | |
|---|---|---|---|
| | C | H | N |
| Calculated (%): | 48.79 | 3.33 | 12.45 |
| Found (%): | 47.15 | 3.49 | 11.89 |

Infrared absorption spectrum (cm$^{-1}$, nujol): 1785, 1760, 1690, 1670, 1610

NMR spectrum (δ, DMSO-d$_6$): 2.35 (3H, s), 2.36 (3H, s), 3.31 (1H, d, J=18 Hz), 3.55 (1H, d, J=18 Hz), 3.91 (3H, s), 4.21 (1H, d, J=12 Hz), 4.42 (1H, d, J=12 Hz), 4.90 (1H, d, J=5 Hz), 5.57 (1H, dd, J=8 Hz, 5 Hz), 5.74 (1H, d, J=8 Hz), 6.73 (2H, d, J=8.5 Hz), 7.26 (2H, d, J=8.5 Hz), 7.87 (1H, s), 8.06 (1H, s), 9.03 (1H, s), 9.32 (1H, d, J=8 Hz), 9.98 (1H, d, J=8 Hz)

EXAMPLE 8

7β-[D-2-(6,7-Diacetoxychromone-3-carboxamido)-2-(4-hydroxyphenyl)acetamido]-3-[(5-methyl-1,3,4-thiadiazol-2-yl)thiomethyl]-3-cephem-4-carboxylic acid and its sodium salt (a)

7β-[D-2-(6,7-Diacetoxychromone-3-carboxamido)-2-(4-hydroxyphenyl)acetamido]-3-[(5-methyl-1,3,4-thiadiazol-2-yl)thiomethyl]-3-cephem-4-carboxylic acid N,O-Bis(trimethylsilyl)acetamide (1 M solution in dichloromethane 2.5 ml) was added dropwise to a stirred suspension of 7β-[D-2-amino-2-(4-hydroxyphenyl)acetamido]-3-[(5-methyl-1,3,4-thiadiazol-2-yl)thiomethyl]-3-cephem-4-carboxylic acid (247 mg, 0.5 mmol) in ethyl acetate (8 ml) at 0° C. The solution was stirred for 20 minutes at 0° C., to which was added a solution of the acid chloride (243 mg, 0.75 mmol) described in Example 6-a). After stirring for 4 hours at 0° C., the mixture was diluted with ethyl acetate (150 ml), washed with water (20 ml), 0.5 N hydrochloric acid (20 ml×2), water (20 ml×2) and saturated brine (20 ml×2), dried ($MgSO_4$) and the solvent was evaporated. After the addition of acetone to the residue, the mixture was allowed to stand for 20 hours at room temperature. After removal of the acetone, the residue was triturated with ethyl ether to give the desired compound (211 mg, 54%).

Melting point: 190°–205° C. (decomposition)

| Elemental analysis: for $C_{33}H_{27}N_5O_{12}S_3$ | | | |
|---|---|---|---|
| | C | H | N |
| Calculated (%): | 50.70 | 3.48 | 8.96 |
| Found (%): | 50.84 | 3.34 | 7.55 |

Infrared absorption spectrum ($cm^{-1}$, nujol): 1780, 1720, 1670, 1615

NMR spectrum (δ, DMSO-$d_6$): 2.35 (3H, s), 2.37 (3H, s), 2.69 (3H, s), 3.48 (1H, d, J=18 Hz), 3.70 (1H, d, J=18 Hz), 4.18 (1H, d, J=13 Hz), 4.28 (1H, d, J=13 Hz), 5.03 (1H, d, J=5 Hz), 5.6–5.9 (2H, m), 6.73 (2H, d, J=8.5 Hz), 7.26 (2H, d, J=8.5 Hz), 7.87 (1H, s), 8.06 (1H, s), 9.03 (1H, s), 9.40 (1H, d, J=8 Hz), 9.99 (1H, d, J=8 Hz)

(b) Sodium salt of the compound described in (a)

According to the process described in Example 6-b), the desired compound (140 mg, 88%) was obtained from the compound (155 mg, 0.198 mmol) described in (a).

Melting point: about 250° C. (decomposition)

| Elemental analysis: for $C_{33}H_{26}N_5NaO_{12}S_3$ | | | |
|---|---|---|---|
| | C | H | N |
| Calculated (%): | 49.31 | 3.26 | 8.71 |
| Found (%): | 46.82 | 3.49 | 8.06 |

Infrared absorption spectrum ($cm^{-1}$, nujol): 1760–1785, 1660–1685, 1615

NMR spectrum (δ, DMSO-$d_6$): 2.35 (3H, s), 2.36 (3H, s), 2.66 (3H, s), 3.28 (1H, d, J=18 Hz), 3.54 (1H, d, J=18 Hz9, 4.30 (1H, d, J=12 Hz), 4.54 (1H, d, J=12 Hz), 4.90 (1H, d, J=5 Hz), 5.56 (1H, dd, J=8 Hz, 5 Hz), 5.73 (1H, d, J=8 Hz), 6.71 (2H, d, J=8 Hz), 7.24 (2H, d, J=8 Hz), 7.85 (1H, s), 8.04 (1H, s), 9.01 (1H, s), 9.30 (1H, d, J=8 Hz), 9.97 (1H, d, 8 Hz)

EXAMPLE 9

7β-[D-2-(7,8-Dihydroxychromone-3-carboxamido)-2-(4-hydroxyphenyl)acetamido]-3-[(1-methyltetrazol-5-yl)thiomethyl]-3-cephem-4-carboxylic acid (a) 7,8-Dihydroxychromone-3-carbonyl chloride A mixture of 7,8-dihydroxychromone-3-carboxylic acid (6.6 g, 30 mmol) and thionyl chloride (25 ml) was refluxed for one hour, and the thionyl chloride was removed. After the addition of benzene to the residue, the mixture was evaporated to dryness and the residue was triturated with n-hexane to give the desired compound (7.2 g).

Infrared absorption spectrum ($cm^{-1}$, nujol): 1775, 1660, 1620

(b)

7β-[D-2-(7,8-Dihydroxychromone-3-carboxamido)-2-(4-hydroxyphenyl)acetamido]-3-[(1-methyltetrazol-5-yl)thiomethyl]-3-cephem-4-carboxylic acid According to the process described in Example 3-a), 7β-[D-2-amino-2-(4-hydroxyphenyl)acetamido]-3-[(1-methyltetrazol-5-yl)thiomethyl]-3-cephem-4-carboxylic acid (133 mg, 0.28 mmol) was treated with the acid chloride (60.1 mg, 0.25 mmol) described in (a) to give the desired compound (37 mg, 22%).

Melting point: about 220° C. (with decomposition

| Elemental analysis: for $C_{28}H_{23}N_7O_{10}S_2$ | | | |
|---|---|---|---|
| | C | H | N |
| Calculated (%): | 49.33 | 3.40 | 14.39 |
| Found (%): | 48.08 | 3.19 | 9.55 |

Infrared absorption spectrum ($cm^{-1}$, nujol): 1770, 1660, 1620

NMR spectrum (δ, DMSO-$d_6$): 3.52 (1H, d, J=18 Hz), 3.71 (1H, d, J=18 Hz), 3.93 (3H, s), 4.20 (1H, d, J=13 Hz), 4.35 (1H, d, J=13 Hz), 5.02 (1H, d, J=5 Hz), 5.6–5.9 (2-H, m), 6.73 (2H, d, J=8 Hz), 7.05 (1H, d, J=9 Hz), 7.26 (2H, d, H=8 Hz), 7.52 (1H, d, J=9 Hz), 8.92 (1H, s), 9.38 (1H, d, J=8 Hz), 9.44 (1H, br.s), 9.73 (1H, br.s), 10.20 (1H, d, J=8 Hz), 10.68 (1H, br.s)

EXAMPLE 10

7β-[D-2-(7,8-Diacetoxychromone-3-carboxamido)-2-phenyl-acetamido]-3-[(5-methyl-1,3,4-thiadiazol-2-yl)thiomethyl]-3-cephem-4-carboxylic acid (a) 7,8-Diacetoxychromone-3-carbonyl chloride A mixture of 7,8-diacetoxychromone-3-carboxylic acid (9.5 g, 31 mmol), thionyl chloride (2.6 ml), dimethylformamide (0.1 ml) and benzene (300 ml) was refluxed for 1.5 hours. After the addition of thionyl chloride (2.6 ml) was dimethylformamide (0.1 ml), the mixture was refluxed for a further one hour and evaporated to dryness. The residue was triturated with n-hexane to give the desired compound (9.3 g).

Infrared absorption spectrum ($cm^{-1}$, nujol): 1780, 1770, 1670, 1620

(b)

7β-[D-2-(7,8-Diacetoxychromone-3-carboxamido)-2-phenylacetamido]-3-[5-methyl-1,3,4l-thiadiazol-2-yl)thiomethyl]-3-cephem-4-carboxylic acid N,O-Bis(trimethylsilyl)acetamide (1 M solution in dichloromethane, 5 ml) was added dropwise to a stirred suspension of 7β-(D-2-amino-2-phenylacetamido)-3-[(5-methyl-1,3,4-thiadiazol-2-yl)thiomethyl]-3-cephem-4-carboxylic acid (239 mg, 0.5 mmol) in ethyl acetate (5 ml) at 0° C. The mixture was stirred for one hour at 0° C., to which was added the acid chloride (162 mg, 0.5 mmol) described in (a). After stirring for 4 hours at 0° C., the solution was diluted with ethyl acetate (150 ml), washed successively with water (20 ml), 0.5 N hydrochloric acid (20 ml×2), water (20 ml×2) and saturated brine (20 ml×2), dried (MgSO4) and the solvent was evaporated to dryness to give yellow crystals (190 mg). A portion (114 mg) of the crystals was purified by preparative thin layer chromatography on silica gel (developing solvent: chloroform/methanol/formic acid=90:10:4) to give the desired compound (26 mg).

Melting point: 165°–170° C. (decomposition)

| Elemental analysis: for $C_{33}H_{27}N_5O_{11}S_3$ | | | |
|---|---|---|---|
| | C | H | N |
| Calculated (%): | 51.76 | 3.55 | 9.15 |
| Found (%): | 50.36 | 3.49 | 8.10 |

Infrared absorption spectrum (cm$^{-1}$, nujol): 1785, 1670, 1630, 1620

NMR spectrum (δ, DMSO-d$_6$): 2.38 (3H, s), 2.44 (3H, s), 2.68 (3H, s), 3.52 (1H, d, J=18 Hz), 3.66 (1H, d, J=18 Hz), 4.20 (1H, d, J=13 Hz), 4.48 (1H, d, J=13 Hz), 5.03 (1H, d, J=5 Hz), 5.76 (1H, dd, J=5 Hz, 8 Hz), 5.84 (1H, d, J=8 Hz), 7.28–7.48 (5H, m), 7.57 (1H, d, J=8.5 Hz), 8.16 (1H, d, J=8.5 Hz), 9.00 (1H, s), 9.52 (1H, d, J=8 Hz), 10.08 (1H, d, J=8 Hz)

EXAMPLE 11

7β-[D-2-(7,8-Diacetoxychromone-3-carboxamido)-2-(4-hydroxyphenyl)acetamido]-3-[(1-methyltetrazol-5-yl)thiomethyl]-3-cephem-4-carboxylic acid According to the process described in Example 3-a), 7β-[D-2-amino-2-(4-hydroxphenyl)acetamido]-3-[(1-methyltetrazol-5-yl)thiomethyl]-3-cephem-4-carboxylic acid (133 mg, 0.28 mmol) was treated with the acid chloride (81.2 mg, 0.25 mmol) described in Example 10-a) to obtain the desired compound (126 mg, 66%).

Melting point: about 180° C. (decomposition)

| Elemental analysis: for $C_{32}H_{27}N_7O_{12}S_2$ | | | |
|---|---|---|---|
| | C | H | N |
| Calculated (%): | 50.19 | 3.55 | 12.81 |
| Found (%): | 48.24 | 3.53 | 9.91 |

Infrared absorption spectrum (cm$^{-1}$, nujol): 1780, 1665, 1610

NMR spectrum (δ, DMSO-d$_6$): 2.38 (3H, s), 2.45 (3H, s), 3.62 (2H, br), 3.92 (3H, s), 4.21 (1H, d, J=13 Hz), 4.37 (1H, d, J=13 Hz), 5.02 (1H, d, J=4.5 Hz), 5.62–5.85 (2H, m), 6.74 (2H, d, J=8.5 Hz), 7.27 (2H, s, J=8.5 Hz), 7.58 (1H, d, J=9 Hz), 8.16 (1H, d, J=9 Hz), 9.02 (1H, s), 9.40 (1H, d, J=8 Hz), 9.45 (1H, br.s), 9.96 (1H, d, J=8 Hz)

EXAMPLE 12

7β[D-2-(7,8-Diacetoxychromone-3-carboxamido)-2-(4-hydroxyphenyl)acetamido]-3-[(5-methyl-1,3,4-thiadiazol-2-yl)thiomethyl]-3-cephem-4-carboxylic acid N,O-Bis(trimethylsilyl)acetamide (1 M solution in dichloromethane, 2 ml) was added dropwise to a stirred suspension of 7β-[D-2-amino-2-(4-hydroxyphenyl)acetamido]-3-[(5-methyl-1,3,4-thiadiazol-2-yl)thiomethyl-3-cephem-4-carboxylic acid (98.6 mg, 0.2 mmol) in ethyl acetate (3 ml) at 0° C. The mixture was stirred for one hour at 0° C., to which was added the acid chloride (32.5 mg, 0.2 mmol) described in Example 10-a). After stirring for 4 hours at 0° C., the mixture was diluted with ethyl acetate (60 ml), washed successively with water (20 ml), 0.5 N hydrochloric acid (10 ml×2), water (10 ml) and saturated brine (10 ml×2), dried (MgSO4) and the solvent was evaporated. After the addition of acetone (10 ml) to the residue, the mixture was allowed to stand for 11 hours at 20° C. After removal of the solvent, the residue was triturated with ethyl ether to give yellow crystals (98 mg). A portion (86 mg) of the crystals was purified by preparative thin layer chromatography on solica gel (developing solvent: chloroform/methanol/formic acid=98:10:4) to give the desired compound (17 mg).

Melting point: 180°–185° C. (decomposition)

| Elemental analysis: for $C_{33}H_{27}N_5O_{12}S_3$ | | | |
|---|---|---|---|
| | C | H | N |
| Calculated (%): | 50.70 | 3.48 | 8.96 |
| Found (%): | 49.67 | 3.60 | 7.73 |

Infrared absorption spectrum (cm$^{-1}$, nujol): 1780, 1665, 1630, 1615

NMR spectrum (δ, DMSO-d$_6$): 2.38 (3H, s), 2.44 (3H, s), 2.68 (3H, s), 3.52 (1H, d, J=18 Hz), 3.68 (1H, d, J=18 Hz), 4.20 (1H, d, J=13 Hz), 4.48 (1H, d, J=13 Hz), 5.02 (1H, d, J=4.5 Hz), 5.68 (1H, d, J=8 Hz), 5.76 (1H, dd, J=4.5 Hz, 8 Hz), 6.73 (2H, d, J=8 Hz), 7.25 (2H, d, J=8 Hz), 7.56 (1H, d, J=8.5 Hz), 8.14 (1H, d, J=8.5 Hz), 9.00 (1H, s), 9.39 (1H, d, J=8 Hz), 9.44 (1H, s), 9.95 (1H, d, J=8 Hz)

EXAMPLE 13

7β-[D-2-(7-Hydroxychromone-3-carboxamido)-2-(4-hydroxyphenyl)acetamido]-3-[(1-methyltetrazol-5-yl)thiomethyl]-3-cephem-4-carboxylic acid In accordance with the procedure described in Example 5-a), 7-hydroxychromone-3-carboxylic acid (206 mg, 1 mmol) was treated with thionyl chloride (0.3 ml, 4.1 mmol) to obtain 7-hydroxychromone-3-carbonyl chloride.

N,O-Bis(trimethylsilyl)acetamide (3 ml) was added to a stirred suspension of 7β-[D-2-amino-2-(4-hydroxyphenyl) acetamido]-3-[(1-methyltetrazol-5-yl)-thiomethyl]-3-cephem-4-carboxylic acid (157 mg, 0.33 mmol) in ethyl acetate (20 ml). The whole amount of the acid chloride described above was added to the above ice-cooled mixture, and the mixture was stirred at room temperature overnight. The reaction mixture was washed successively with ice-water (15 ml), 0.5 N hydrochloric acid (15 ml) and water (15 ml) and dried (MgSO4). After removal of the solvent, the residue was dissolved in ethyl acetate (3 ml), to which ethyl ether (100 ml) was added.

The precipitate was filtered off to give the desired compound (23.7 mg, 11%).

Melting point: 180°–187° C. (decomposition)

| Elemental analysis: for $C_{28}H_{23}N_7O_9S_2$ | | | |
|---|---|---|---|
| | C | H | N |
| Calculated (%): | 50.52 | 3.48 | 14.73 |
| Found (%): | 44.41 | 3.82 | 11.65 |

Infrared absorption spectrum (cm$^{-1}$, nujol): 1770, 1690, 1660, 1610

NMR spectrum (δ, acetone-d$_6$): 3.72 (2H, s), 3.98 (3H, s), 4.40 (2H, s), 5.16 (1H, d, J=6 Hz), 5.84 (1H, d, J=9 Hz), 5.88 (1H, dd, J=11 Hz, 6 Hz), 6.83 (1H, d, J=9 Hz), 7.42 (1H, d, J=9 Hz), 6.85–9.18 (3H, m), 8.82 (1H, s), 8.37 (1H, d, J=10 Hz), 10.36 (1H, d, J=10 Hz)

EXAMPLE 14

7β-[D-2-(6-Acetoxychromone-3-carboxamido)-2-(4-hydroxyphenyl)acetamido]-3-[(1-methyltetrazol-5-yl)thiomethyl]-3-cephem-4-carboxylic acid In accordance with the procedure described in Example 5-a), 6-acetoxychromone-3-carboxylic acid (77 mg, 0.314 ml) was treated with thionyl chloride (0.1 ml, 1.4 mmol) to obtain 6-acetoxychromone-3-carbonyl chloride.

N,O-Bis(trimethylsilyl)acetamide (3 ml) was added to a stirred suspension of 7β-[D-2-amino-2-(4-hydroxyphenyl)acetamido]-3-[(1-methyltetrazol-5-yl)thiomethyl]-3-cephem-4-carboxylic acid (150 mg, 0.314 mmol) in ethyl acetate (20 ml). The whole amount of the acid chloride described above was added to the above ice-cooled mixture, and the mixture was stirred at room temperature overnight. The reaction mixture was washed successively with ice-water (15 ml), 0.5 N hydrochloric acid (15 ml) and water (15 ml) and dried (MgSO$_4$). After removal of the solvent, the residue was dissolved in ethyl acetate (3 ml), and ethyl ether (100 ml) was added to the solution. The precipitate was filtered off to give the desired compound (17.2 mg, 8%).

Melting point: 191°–195° C. (decomposition)

| Elemental analysis: for $C_{30}H_{25}N_7O_{10}S_2$ | | | |
|---|---|---|---|
| | C | H | N |
| Calculated (%): | 50.92 | 3.56 | 13.85 |
| Found (%): | 45.66 | 3.83 | 10.01 |

Infrared absorption spectrum (cm$^{-1}$, nujol): 1780, 1760, 1690, 1660, 1620

NMR spectrum (δ, acetone-d$_6$): 2.35 (3H, s), 3.71 (2H, s), 3.99 (3H, s), 4.38 (2H, s), 5.08 (1H, d, J=5 Hz), 5.80 (1H, dd, J=5 Hz, 12 Hz), 5.88 (1H, d, J=9 Hz), 6.83 (2H, d, J=10 Hz), 7.42 (2H, d, J=10 Hz), 7.1–8.05 (3H, m), 8.96 (1H, s), 8.35 (1H, d, J=10 Hz), 10.12 (1H, d, J=10 Hz)

EXAMPLE 15

7β-[D-2-(Chromone-3-carboxamido)-2-(4-hydroxyphenyl)acetamido]-3-[(1-methyltetrazol-5-yl)thiomethyl]-3-cephem-4-carboxylic acid (a) Chromone-3-carbonyl chloride In accordance with the procedure described in Example 5-a), chromone-3-carboxylic acid (3.8 g, 20 mmol) was treated with thionyl chloride (1.73 ml) to obtain the desired compound (3.76 g, 90%).

Infrared absorption spectrum (cm$^{-1}$, nujol): 1785, 1650, 1618

(b)
7β-[D-2-(Chromone-3-carboxamido)-2-(4-hydroxyphenyl)acetamido]-3-[(1-methyltetrazol-5-yl)thiomethyl]-3-cephem-4-carboxylic acid In accordance with the procedure described in Example 3-a), 7β-[D-2-amino-2-(4-hydroxyphenyl)acetamido]-3-[(1-methyltetrazol-5-yl)thiomethyl]-3-cephem-4-carboxylic acid (133 mg, 0.28 mmol) was treated with the acid chloride (52.1 mg, 0.25 mmol) described in (a) to obtain the desired compound (57 mg, 35%).

Melting point: about 170° C. (decomposition)

| Elemental analysis: for $C_{28}H_{23}N_7O_8S_2$ | | | |
|---|---|---|---|
| | C | H | N |
| Calculated (%): | 51.76 | 3.57 | 15.09 |
| Found (%): | 51.69 | 3.49 | 11.92 |

Infrared absorption spectrum (cm$^{-1}$, nujol): 1780, 1660, 1610

NMR spectrum (δ, DMSO-d$_6$): 3.52 (1H, d, J=18 Hz), 3.72 (1H, d, J=18 Hz), 3.92 (3H, s), 4.21 (1H, d, J=13 Hz), 4.36 (1H, d, J=13 Hz), 5.02 (1H, d, J=4.5 Hz), 5.64–5.84 (2H, m), 6.73 (2H, d, J=8 Hz), 7.27 (2H, d, J=8 Hz), 7.41–8.1 (3H, m), 8.21 (1H, d, J=8 Hz), 9.04 (1H, s), 9.40 (1H, d, J=18 Hz), 9.44 (1H, br.s), 10.08 (1H, d, J=8 Hz)

EXAMPLE 16

7β-[D-2-(Chromone-3-carboxamido)-2-phenylacetamido]-3-[(1-methyltetrazol-5-yl)thiomethyl]-3-cephem-4-carboxylic acid (a)
7β-[D-2-(Chromone-3-carboxamido)-2-phenylacetamido]-3-acetoxymethyl-3-cephem-4-carboxylic acid N,O-Bis(trimethylsilyl)acetamide (7.91 ml, 32 mmol) was added to a stirred suspension of cephaloglycin (3.244 g, 8 mmol) in dichloromethane (65 ml) at 0° C., and the mixture was stirred for 20 minutes at 0° C. A solution of the acid chloride (1.67 g, 8 mmol) described in Example 15-a) in dichloromethane (40 ml) was added dropwise to the above mixture with stirring at 0° C., and stirring was continued for 30 minutes at 0° C., and for a further 15 minutes at room temperature. The solvent was evaporated and the residue was dissolved in ethyl acetate (1 liter). The resulting solution was washed successively with 0.5 N hydrochloric acid, water and saturated brine, dried (MgSO$_4$) and evaporated to dryness. The residue was triturated with ethyl ether to give the desired compound (2.56 g, 55%).

Melting point: about 170°–200° C. (decomposition)

Infrared absorption spectrum (cm$^{-1}$, nujol): 1788, 1740, 1720, 1665, 1615

(b)
7β-[D-2-(Chromone-3-carboxamido)-2-phenylacetamido]-3-[(1-methyltetrazol-5-yl)thiomethyl]-3-cephem-4-carboxylic acid A mixture of the compound (250 mg, 0.433 mmol) described in (a), 5-mercapto-1-methyltetrazol (76 mg, 0.65 mmol), sodium hydrogen carbonate (91 mg) and phosphate buffer (pH 6.4, 9 ml) was stirred at 60°–70° C. for 3.5 hours. The reaction solution was acidified with 1 N hydrochloric acid, and the mixture was extracted with ethyl acetate. The extract was washed with water and dried (MgSO$_4$), and the solvent was removed. The residue was triturated with ethyl ether to give powder (81 mg), which was further purified by thin layer chromatography on silica gel (developing solvent: benzene/dioxane/acetic acid=4:1:1) to obtain the desired compound (7.6 mg).

Melting point: 175°–178° C. (decomposition)

Infrared absorption spectrum (cm$^{-1}$, nujol): 1780, 1660, 1620, 1610

NMR spectrum (δ, acetone-d$_6$): 3.71 (2H, s), 3.95 (3H, s), 4.38 (2H, s), 5.06 (1H, d, J=5 Hz), 5.90 (1H, dd, J=5 Hz, 10 Hz), 6.00 (1H, d, J=8 Hz), 7.12–8.26 (9H, m), 8.46 (1H, d, J=10 Hz), 8.92 (1H, s), 11.38 (1H, d, J=8 Hz)

EXAMPLE 17

7β-[D-2-(6,7-Dihydroxychromone-3-carboxamido)-2-phenylacetamido]-3-[(1-methyltetrazol-5-yl)thiomethyl]-3-cephem-4-carboxylic acid Sodium hydrogen carbonate (1 M solution, 518 μl) was added to a mixture of the compound (200 mg, 0.259 mmol) described in Example 5-c) in water (15 ml), and the resulting mixture was allowed to stand at room temperature for 43 hours. This solution was adjusted to pH 2 with 1 N hydrochloric acid, and extracted with ethyl acetate (200 ml). The extract was washed with water and saturated brine and dried (MgSO$_4$). The solvent was evaporated and the residue was triturated with ethyl ether to give the desired compound (134 mg, 78%).

This compound was confirmly identified with the compound described in Example 1-b) by NMR, IR and thin layer chromatography.

EXAMPLE 18

7β-[D-2-(6,7-Diacetoxychromone-3-carboxamido)-2-phenylacetamido]-3-[(1-methyltetrazol-5-yl)thiomethyl]-3-cephem-4-carboxylic acid (a)

D-2-(6,7-Diacetoxychromone-3-carboxamido)-2-phenylacetic acid

A mixture of D-phenylglycin (6.6 g, 44 mmol) and hexamethyldisilazane (28.4 g) was refluxed for 10 hours with stirring, and the solvent was removed. The residue was dissolved in dichloromethane (120 ml), to which were added N,N-dimethylaniline (5.3 g) and 6,7-diacetoxychromone-3-carbonyl chloride (13.0 g, 40 mmol) described in Example 5-a) at 0° C. with stirring.

The mixture was stirred for 10 minutes at 0° C., and for a further 3 hours at room temperature, and acidified with 1 N hydrochloric acid with cooling.

The precipitate was filtered off, washed successively with water and cold methanol, and dried to afford the desired compound (13.8 g).

Melting point: 210°–212° C.

Infrared absorption spectrum (cm$^{-1}$, nujol): 1770, 1725, 1675, 1615

NMR spectrum (δ, DMSO-d$_6$): 2.33 (6H, s), 5.58 (1H, d, J=7 Hz), 7.34 (5H, s), 7.78 (1H, s), 8.00 (1H, s), 8.98 (1H, s)

(b)

7β-[D-2-(6,7-Diacetoxychromone-3-carboxamido)-2-phenylacetamido]-3-[(1-methyltetrazol-5-yl)-thiomethyl]-3-cephem-4-carboxylic acid N,N-Dimethylaniline (0.665 g) was added to a stirred solution of the compound (2.19 g, 5 mmol) described in (a) in a mixture of dichloromethane (20 ml) and dimethylformamide (4 ml) at 0° C. The mixture was cooled to −18° C., to which was added a solution of ethyl chloroformate (0.57 g) in dichloromethane (5 ml). The mixture was stirred for one hour maintaining the temperature between −15° C. and −10° C. To this solution was added a mixture of 7-amino-3-[(1-methyltetrazol-5-yl)thiomethyl]-3-cephem-4-carboxylic acid (1.14 g, 5 mmol) and N,O-bis(trimethylsilyl)acetamide (5 ml) in acetonitrile (35 ml) at −30° C. The resulting solution was stirred for one hour at temperatures between −10° C. and −5° C., for another hour at 0° C., and for a further one hour at room temperature. The solvent was removed and to the residue was added water (40 ml), followed by 1 N-hydrochloric acid to acidify the mixture. The precipitate was filtered off, washed with water and dried. The crude solid was purified by preparative thin layer chromatography on silica gel (developing solvent: chloroform/methanol/formic acid=95:5:0.5) to obtain the desired compound (1.0 g). This compound was confirmly identified with the compound described in Example 5-b) by NMR, IR and thin layer chromatography.

The following compounds were synthesized in a similar manner as described in Examples 1–18.

EXAMPLE 19

7β-[D-2-(6,7-Dihydroxychromone-3-carboxamido)-2-(4-hydroxyphenyl)acetamido]-3-[(1,3,4-thiadiazol-2-yl)thiomethyl]-3-cephem-4-carboxylic acid Yield: 52.6%

Melting point: 190°–192° C. (decomposition)

Infrared absorption spectrum (cm$^{-1}$, nujol): 1772, 1660, 1615

NMR spectrum (δ, DMSO-d$_6$): 3.60 (2H, br), 4.22 (1H, d, J=12 Hz), 4.56 (1H, d, J=12 Hz), 5.02 (1H, d, J=5 Hz), 5.6–5.8 (2H, m), 6.70 (2H, d, J=9 Hz), 6.97 (1H, s), 7.24 (2H, d, J=9 Hz), 7.40 (1H, s), 8.84 (1H, s), 9.35 (1H, d, J=8 Hz), 9.57 (1H, s), 10.24 (1H, d, J=8 Hz)

EXAMPLE 20

7β-[D-2-(6,7-Dihydroxychromone-3-carboxamido)-2-(4-hydroxyphenyl)acetamido]-3-[(1-ethyltetrazol-5-yl)thiomethyl]-3-cephem-4-carboxylic acid Yield: 64.0%

Melting point: 214°–216° C. (decomposition)

Infrared absorption spectrum (cm$^{-1}$, nujol): 1770, 1664, 1615

NMR spectrum (δ, DMSO-d$_6$): 1.40 (3H, t, J=7 Hz), 3.5–3.8 (2H, m), 4.0–4.3 (2H, m), 5.00 (1H, d, J=5 Hz), 5.29 (2H, q, J=7 Hz), 5.65 (1H, s), 5.70 (1H, m), 6.71 (2H, d, J=8 Hz), 6.97 (1H, s), 7.24 (2H, d, J=8 Hz), 7.41 (1H, s), 8.84 (1H, s), 9.32 (1H, s), 9.42 (1H, s), 10.08 (1H, s), 10.25 (1H, d, J=8 Hz), 10.73 (1H, s)

EXAMPLE 21

7β-[D-2-(6,7-Dihydroxychromone-3-carboxamido)-2-(4-hydroxyphenyl)acetamido]-3-{[1-(2-dimethylaminoethyl)tetrazol-5-yl]-thiomethyl}-3-cephem-4-carboxylic acid Yield: 50.8%
Melting point: 248°–250° C. (decomposition)
Infrared absorption spectrum (cm$^{-1}$, nujol): 1770, 1663, 1615
NMR spectrum (δ, DMSO-d$_6$): 2.51 (6H, s), 3.12 (2H, t, J=6 Hz), 3.5–3.7 (2H, m), 4.1–4.3 (2H, m), 4.53 (2H, t, J=6 Hz), 4.97 (1H, d, J=5 Hz), 5.6–5.8 (2H, m), 6.71 (2H, d, J=8 Hz), 6.97 (1H, s), 7.23 (2H, d, J=8 Hz), 7.40 (1H, s), 8.83 (1H, s), 9.34 (1H, d, J=8 Hz), 10.24 (1H, d, J=7 Hz)

EXAMPLE 22

Sodium salt of
7β-[D-2-(6,7-Dihydroxychromone)-3-carboxamido)-2-(4-hydroxyphenyl)acetamido]-3-[(4H-1,2,4-triazol-3-yl)thiomethyl]-3-cephem-4-carboxylic acid Yield: 51.0%
Melting point: 230°–245° C. (decomposition)
Infrared absorption spectrum (cm$^{-1}$, nujol): 1770, 1660, 1610
NMR spectrum (δ, DMSO-d$_6$): 3.40 (2H, m), 4.64 (1H, d, J=12 Hz), 4.84 (1H, d, J=12 Hz), 4.92 (1H, d, J=5 Hz), 5.56 (2H, m), 6.02 (1H, br.s), 6.68 (2H, d, J=8 Hz), 6.89 (1H, s), 7.16 (2H, d, J=8 Hz), 7.80 (1H, s), 8.48 (1H, s), 8.50 (1H, s), 9.32 (1H, d, J=8 Hz), 10.84 (1H, d, J=8 Hz)

EXAMPLE 23

7β-[D-2-(6,7-Dihydroxychromone-3-carboxamido)-2-(4-hydroxyphenyl)acetamido]-3-[(1-carboxymethyltetrazol-5-yl)thiomethyl]-3-cephem-4-carboxylic acid Yield: 45.5%
Melting point: 230°–231° C. (decomposition)
Infrared absorption spectrum (cm$^{-1}$, nujol): 1770, 1664, 1615
NMR spectrum (δ, DMSO-d$_6$): 3.50 (1H, d, J=18 Hz), 3.72 (1H, d, J=18 Hz) 4.21 (1H, d, J=14 Hz), 4.48 (1H, d, J=14 Hz), 5.00 (1H, d, J=5.5 Hz) 5.30 (2H, s), 5.6–5.9 (2H, m), 6.75 (2H, d, J=9 Hz), 7.00 (1H, s), 7.26 (2H, d, J=9 Hz), 7.44 (1H, s), 8.86 (1H, s), 9.38 (1H, d, J=8 Hz), 10.26 (1H, d, J=7.5 Hz)

EXAMPLE 24

7β-[D-2-(6,7-Dihydroxychromone-3-carboxamido)-2-(4-hydroxyphenyl)acetamido]-3-(2-pyridylthiomethyl)-3-cephem-4-carboxylic acid Yield: 59.0%
Melting point: 218°–220° C. (decomposition)
Infrared absorption spectrum (cm$^{-1}$, nujol): 1764, 1672, 1656, 1612
NMR spectrum (δ, DMSO-d$_6$): 3.1–3.6 (2H, m), 4.1–4.6 (2H, m), 4.89 (1H, d, J=5 Hz), 5.52 (1H, dd, J=5 Hz, 8 Hz), 5.71 (1H, d, J=7 Hz), 6.70 (2H, d, J=9 Hz), 6.87 (1H, s), 7.0–7.2 (1H, m), 7.24 (2H, d, J=9 Hz), 7.31 (1H, s), 7.5–7.7 (1H, m), 7.6–7.9 (1H, m), 8.3–8.5 (1H, m), 8.75 (1H, s), 9.28 (1H, d, J=8 Hz), 10.38 (1H, d, J=8 Hz)

EXAMPLE 25

7β-[D-2-(6,7-Dihydroxychromone-3-carboxamido)-2-(4-hydroxyphenyl)acetamido]-3-[2-(pyridyl-1-oxido)-thiomethyl]-3-cephem-4-carboxylic acid Yield: 45.8%
Melting point: 240°–242° C. (decomposition)
Infrared absorption spectrum (cm$^{-1}$, nujol): 3450, 3300, 1792, 1666, 1620
NMR spectrum (δ, DMSO-d$_6$): 3.4–3.7 (2H, m), 4.0–4.2 (2H, m), 5.06 (1H, d, J=5 Hz), 5.74 (1H, dd, J=5 Hz, 8 Hz), 5.69 (1H, d, J=8 Hz), 6.71 (2H, d, J=9 Hz), 6.98 (1H, s), 7.1–7.5 (3H, m), 7.25 (2H, d, J=9 Hz), 7.41 (1H, s), 8.23–8.34 (1H, m), 8.85 (1H, s), 9.38 (1H, d, J=8 Hz), 9.44 (1H, s), 10.09 (1H, s), 10.27 (1H, d, J=8 Hz), 10.74 (1H, s)

EXAMPLE 26

7β-[D-2-(6,7-Dihydroxychromone-3-carboxamido)-2-(4-hydroxyphenyl)acetamido]-3-(2-pyrimidinylthiomethyl)-3-cephem-4-carboxylic acid Yield: 35.3%
Melting point: 205°–207° C. (decomposition)
Infrared absorption spectrum (cm$^{-1}$, nujol): 1780, 1717, 1662, 1617
NMR spectrum (δ, DMSO-d$_6$): 3.41 (1H, d, J=18 Hz), 3.71 (1H, d, J=18 Hz), 3.91 (1H, d, J=13 Hz), 4.58 (1H, d, J=13 Hz), 5.01 (1H, d, J=5 Hz), 5.6–5.8 (2H, m), 6.71 (2H, d, J=8 Hz), 6.98 (1H, s), 7.21 (1H, t, J=5 Hz), 7.25 (2H, d, J=8 Hz), 7.42 (1H, s), 8.59 (2H, d, J=5 Hz), 8.85 (1H, s), 9.36 (1H, d, J=9 Hz), 9.45 (1H, s), 10.15 (1H, s), 10.27 (1H, d, J=7 Hz), 10.72 (1H, s)

EXAMPLE 27

7β-[D-2-(6,7-Dihydroxychromone-3-carboxamido)-2-(4-hydroxyphenyl)acetoamido]-3-[(5-methyl-1,3,4-oxadiazol-2-yl)thiomethyl]-3-cephem-4-carboxylic acid Yield: 48.5%
Melting point: 227°–229° C. (decomposition)
Infrared absorption spectrum (cm$^{-1}$, nujol): 3440, 3280, 1782, 1720, 1668, 1620
NMR spectrum (δ, DMSO-d$_6$): 2.40 (3H, s), 3.3–3.8 (2H, m), 4.11 (1H, d, J=14 Hz), 4.35 (1H, d, J=14 Hz), 5.00 (1H, d, J=5 Hz), 5.69 (1H, d, J=8 Hz), 5.72 (1H, dd, J=5 Hz, 8 Hz), 6.72 (2H, d, J=8 Hz), 6.99 (1H, s), 7.24 (2H, d, J=8 Hz), 7.41 (1H, s), 8.84 (1H, s), 9.36 (1H, d, J=8 Hz), 10.25 (1H, d, J=8 Hz)

EXAMPLE 28

7β-[D-2-(6,7,8-Trihydroxychromone-3-carboxamido)-2-(4-hydroxyphenyl)acetamido]-3-[(1-methyltetrazol-5-yl)thiomethyl]-3-cephem-4-carboxylic acid Yield: 80%
Melting point: 196°–202° C. (decomposition)
Infrared absorption spectrum (cm$^{-1}$, nujol): 1770, 1655, 1610
NMR spectrum (δ, DMSO-d$_6$): 3.53 (1H, d, J=17 Hz), 3.67 (1H, d, J=17 Hz), 3.92 (3H, s), 4.19 (1H, d, J=14 L Hz), 4.37 (1H, d, J=14 L Hz), 5.00 (1H, d, J=5 Hz), 5.63–5.81 (2H, m), 6.71 (2H, d, J=10 Hz), 7.03 (1H, s), 7.25 (2H, d, J=10 Hz), 8.87 (1H, s), 9.37 (1H, d, J=10 Hz), 9.42 (1H, s), 9.75 (1H, br.s), 9.90 (1H, br.s), 10.15 (1H, br.s), 10.26 (1H, d, J=8 Hz)

EXAMPLE 29

7β-[D-2-(6,7,8-Triacetoxychromone-3-carboxamido)-2-(4-hydroxyphenyl)acetamido]-3-[(1-methyltetrazol-5-yl)thiomethyl]-3-cephem-4-carboxylic acid Yield: 92%

Melting point: 182°–186° C. (decomposition)

Infrared absorption spectrum (cm$^{-1}$, nujol): 1780, 1665, 1610

NMR spectrum (δ, DMSO-d$_6$): 2.35 (3H, s), 2.41 (3H, s), 2.46 (3H, s), 3.56 (1H, d, J=18 Hz), 3.66 (1H, d, J=18 Hz), 3.92 (3H, s), 4.19 (1H, d, J=13 Hz), 4.37 (1H, d, J=13 Hz), 5.00 (1H, d, J=4.5 Hz), 5.62–5.81 (2H, m), 6.60 (2H, d, J=10 Hz), 7.24 (2H, d, J=10 Hz), 8.02 (1H, s), 9.00 (1H, s), 9.37 (1H, d, J=10 Hz), 9.42 (1H, s), 9.87 (1H, d, J=8 Hz)

EXAMPLE 30

7β-[D-2-(6,7,8-Trihydroxychromone-3-carboxamido)-2-(4-hydroxyphenyl)acetamido]-3-[(1-carboxymethyltetrazol-5-yl)thiomethyl]-3-cephem-4-carboxylic acid Yield: 57%

Melting point: 212°–220° C. (decomposition)

Infrared absorption spectrum (cm$^{-1}$, nujol): 1770, 1660, 1610

NMR spectrum (δ, DMSO-d$_{6L}$): 3.42–3.48 (2H, m), 4.18 (1H, d, J=13 Hz), 4.43 (1H, d, J=13 Hz), 4.97 (1H, d, J=5 Hz), 5.27 (2H, s), 5.57–5.80 (2H, m), 6.74 (2H, d, J=8 Hz), 7.06 (1H, s), 7.25 (2H, d, J=8 Hz), 8.85 (1H, s), 9.47 (1H, d, J=10 Hz), 10.25 (1H, d, J=8 Hz)

EXAMPLE 31

7β-[D-2-(6,7,8-Triacetoxychromone-3-carboxamido)-2-(4-hydroxyphenyl)acetamido]-3-[(1-carboxymethyltetrazol-5-yl)thiomethyl]-3-cephem-4-carboxylic acid Yield: 74%

Melting point: 206°–208° C. (decomposition)

Infrared absorption spectrum (cm$^{-1}$, nujol): 1780, 1740, 1665, 1610

NMR spectrum (δ, DMSO-d$_6$): 2.36 (3H, s), 2.41 (3H, s), 2.45 (3H, s), 3.42–3.80 (2H, m), 4.20 (1H, d, J=14 L Hz), 4.46 (1H, d, J=14 Hz), 4.99 (1H, d, J=5 Hz), 5.40 (2H, s), 5.59–5.85 (2H, m), 6.64 (2H, d, J=8 Hz), 7.25 (2H, d, J=8 Hz), 8.03 (1H, s), 9.01 (1H, s), 9.40 (2H, d, J=10 Hz), 9.46 (1H, s), 9.90 (1H, d, J=8 Hz)

EXAMPLE 32

Sodium salt of 7β-[D-2-(6-Hydroxy-7-sodiooxychromone-3-carboxamido)-2-(4-hydroxyphenyl)acetamido]-3-[(1-methyltetrazol-5-yl)thiomethyl]-3-cephem-4-carboxylic acid Yield: 68.2%

Melting point: about 240° C. (decomposition)

Infrared absorption spectrum (cm$^{-1}$, nujol): 1755, 1655, 1605

NMR spectrum (δ, DMSO-d$_6$): 3.32 (1H, d, J=18 Hz), 3.55 (1H, d, J=18 Hz), 3.91 (3H, s), 4.22 (1H, d, J=12 Hz), 4.46 (1H, d, J=12 Hz), 4.90 (1H, d, J=5 Hz), 5.58 (1H, dd, J=8 Hz, 5 Hz), 5.69 (1H, d, J=8 Hz), 6.11 (1H, s), 6.73 (2H, d, J=8.5 Hz), 6.99 (1H, s), 7.24 (2H, d, J=8.5 Hz), 8.63 (1H, s)

EXAMPLE 33

Sodium salt of 7β-[D-2-(6-Hydroxy-7-sodiooxychromone-3-carboxamido)-2-(4-hydroxyphenyl)acetamido]-3-[(5-methyl-1,3,4-thiadiazol-2-yl)thiomethyl]-3-cephem-4-carboxylic acid Yield: 84%

Melting point: about 230° C. (decomposition)

Infrared absorption spectrum (cm$^{-1}$, nujol): 1765, 1665, 1615

NMR spectrum (δ, DMSO-d$_6$): 2.67 (3H, s), 3.28 (1H, d, J=18 Hz), 3.48 (1H, d, J=18 Hz), 4.34 (1H, d, J=14 Hz), 4.52 (1H, d, J=14 Hz), 4.90 (1H, d, J=5 Hz), 5.54 (1H, m), 5.68 (1H, d, J=8 Hz), 6.08 (1H, s), 6.72 (2H, d, J=8.5 Hz), 6.95 (1H, s), 7.23 (2H, d, J=8.5 Hz), 8.51 (1H, s)

EXAMPLE 34

Disodium salt of 7β-[D-2-(6,7-dihydroxychromone-3-carboxamido)-2-(4-hydroxyphenyl)-acetamido]-3-[(1-carboxymethyltetrazol-5-yl)-thiomethyl]-3-cephem-4-carboxylic acid Yield: 83%

Melting point: 220°–250° C. (decomposition)

Infrared absorption spectrum (cm$^-$, nujol): 1760, 1655, 1605

NMR spectrum (δ, DMSO-d$_6$): 3.36 (1H, d, J=18 Hz), 3.56 (1H, d, J=18 Hz), 4.17 (1H, d, J=12 Hz), 4.37 (1H, d, J=12 Hz), 4.66 (2H, br.s), 4.91 (1H, d, J=5 Hz), 5.5–5.8 (2H, m), 6.73 (2H, d, J=8.5 Hz), 6.96 (1H, s), 7.25 (2H, d, J=8.5 Hz), 7.36 (1H, s), 8.78 (1H, s)

The compounds obtained in these examples were tested for their antibacterial activities in vitro.

METHOD

Minimal inhibitory concentration (MIC) was determined by the standard agar dilution method of the Japan Society of Chemotherapy.

Compounds were dissolved in appropriate solvents (sterilized water for sodium salts and acetone-water [1:1] for free acids) and serial two-fold dilutions were made. Sodium salt of Cefazolin was chosen as the control compound.

One-ml aliquots of each dilution were mixed with 9 ml of Mueller Hinton agar in petri-dishes to make agar plates containing the compound at serially diluted concentrations. After agar hardened, plates were put in an incubator at 37° C. for 1.5–2 hours with the lids slightly open to evaporate acetone off the plates.

Test organisms were grown for 18 hours at 37° C. in Trypticase Soy broth and diluted in saline to approximately 10$^6$ colony forming units per ml. A loopful of each cell suspension was applied on the agar plate mentioned above and the plates were incubated for 18 hours at 37° C. before MIC was determined.

MIC values of the compounds of Examples 1, 2, 4, 5, 6, 8 and 22 were determined as their sodium salts and those of other compounds as free carboxylic acids.

The results are shown in Table 2.

TABLE 2

| Test bacteria / Test compound | Staphylococcus aureus 209-P | Escherichia coli NIHJ | Klebsiella pneumoniae EK-6 | Proteus morganii EP-14 | Pseudomonas aeruginosa EP-172 | Serratia marcescens ES-75 |
|---|---|---|---|---|---|---|
| Example 1 | 1.56 | 0.4 | ≦0.1 | 0.4 | 0.8 | ≦0.1 |
| 2 | 1.56 | 0.8 | ≦0.1 | 0.8 | 3.13 | ≦0.1 |
| 3 | 0.8 | 0.2 | ≦0.1 | 0.4 | 0.4 | ≦0.1 |
| 4 | 1.56 | 0.8 | ≦0.1 | 1.56 | 1.56 | ≦0.1 |
| 5 | 1.56 | 0.2 | ≦0.1 | 0.4 | 0.4 | ≦0.1 |
| 6 | 1.56 | 0.8 | ≦0.1 | 0.8 | 3.13 | ≦0.1 |
| 7 | 1.56 | ≦0.1 | ≦0.1 | 0.4 | 0.4 | ≦0.1 |
| 8 | 3.13 | 0.8 | ≦0.1 | 1.56 | 1.56 | ≦0.1 |
| 9 | 0.8 | 1.56 | ≦0.1 | 12.5 | 6.25 | 3.13 |
| 10 | 0.8 | 0.8 | ≦0.1 | 1.56 | 1.56 | 0.2 |
| 11 | 0.8 | 0.8 | ≦0.1 | 25 | 6.25 | 1.56 |
| 12 | 1.56 | 1.56 | ≦0.1 | 3.13 | 1.56 | 0.2 |
| 13 | 0.4 | 6.25 | 12.5 | 25 | 50 | 12.5 |
| 15 | 0.4 | 6.25 | 12.5 | 25 | 100 | 25 |
| 16 | ≦0.1 | 6.25 | 6.25 | 6.25 | 25 | 3.13 |
| 19 | 0.8 | 0.4 | ≦0.1 | 12.5 | 0.4 | 0.2 |
| 20 | 0.8 | 0.2 | ≦0.1 | 3.13 | 0.2 | ≦0.1 |
| 21 | 1.56 | 0.4 | ≦0.1 | 12.5 | 0.8 | ≦0.1 |
| 22 | 3.13 | 1.56 | ≦0.1 | 50 | 1.56 | 0.4 |
| 23 | 3.13 | 0.4 | ≦0.1 | 12.5 | 0.8 | ≦0.1 |
| 24 | 0.8 | 0.4 | ≦0.1 | 25 | 0.8 | ≦0.1 |
| 25 | 1.56 | 0.8 | ≦0.1 | 25 | 0.8 | 0.2 |
| 26 | 0.8 | 0.8 | ≦0.1 | 50 | 1.56 | 0.2 |
| 27 | 0.8 | 0.4 | ≦0.1 | 50 | 1.56 | 0.2 |
| 28 | 3.13 | 3.13 | ≦0.1 | 50 | 0.4 | 0.8 |
| 29 | 1.56 | 1.56 | ≦0.1 | 12.5 | 0.4 | 0.4 |
| 30 | 12.5 | 0.8 | ≦0.1 | 50 | 0.8 | 0.8 |
| 31 | 12.5 | 0.8 | ≦0.1 | 25 | 0.8 | 0.8 |
| Control (Sodium salt of Cefazolin) | 0.4 | 1.56 | 1.56 | >100 | >100 | >100 |

EXAMPLE 35

| Formulation of the tablet | |
|---|---|
| The compound of the Example 3-b) | 250 mg |
| Crystallized cellulose | 80 mg |
| Calcium salt of carboxymethyl-cellulose | 38 mg |
| Calcium stearate | 2 mg |
| One tablet | 370 mg |

The tablets were prepared using the above formulation by conventional processes.

What is claimed is:

1. A cephalosporin compound of the formula:

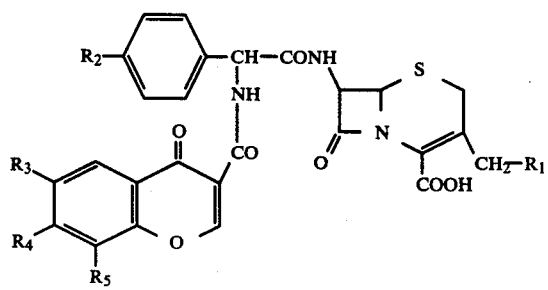

wherein $R_1$ represents a nitrogen-containing heterocyclic-thio group, the nitrogen-containing heterocyclic group of which is selected from the group consisting of pyrrolyl, pyridyl and its N-oxide, imidazolyl, pyrazolyl, pyrimidinyl, pyridazinyl, 1H-1,2,4-triazolyl, 4H-1,2,4-triazolyl, 1H-1,2,3-triazolyl, 2H-1,2,3-triazolyl, 1H-tetrazolyl, 2H-tetrazolyl, thiazolyl, 1,2,3-thiadiazolyl, 1,2,4-thiadiazolyl, 1,3,4-thiadiazolyl, oxazolyl, 1,3,4-oxadiazolyl, 1,2,5-oxadiazolyl, morpholino, benzothiazolyl, and benzoxazolyl, said heterocyclic groups being unsubstituted or substituted by methyl, ethyl, propyl, isopropyl, amino, dimethylaminoethyl, dimethylaminomethyl, diethylaminoethyl, carboxymethyl or carboxyethyl, $R_2$ represents hydrogen or hydroxy, and $R_3$, $R_4$ and $R_5$ each represents hydrogen, hydroxy, acetoxy, propionyloxy or benzyloxy or a pharmaceutically acceptable salt thereof.

2. A compound according to claim 1, wherein $R_1$ is (1-methyltetrazol-5-yl)thio or (5-methyl-1,3,4-thiadiazol-2-yl)thio.

3. A compound according to claim 1, wherein $R_1$ is (1-carboxymethyltetrazol-5-yl)thio.

4. A compound according to claim 2 wherein said compound is 7β-[D-2-(6,7-dihydroxychromone-3-carboxamido)-2-phenylacetamido]-3-[(1methylltetrazol-5-yl)thiomethyl]-3-cephem-4-carboxylic acid or pharmaceutically acceptable salt thereof.

5. A compound according to claim 2 wherein said compound is 7β-[D-2-(6,7-dihydroxychromone-3-carboxamido)-2-phenylacetamido]-3-[(5-methyl-1,3,4-thiadiazol-2-yl) thiomethyl]-3-cepham-4-carboxylic acid or pharmaceutically acceptable salt thereof.

6. A compound according to claim 2 wherein said compound is 7β-[D-2-(6,7-dihydroxychromone-3-carboxamido)-2-(4-hydroxyphenyl)acetamido]-3-[(1-methyltetrazol-5-yl)thiomethyl]-3-cephem-4-carboxylic acid or pharmaceutically acceptable salt thereof.

7. A compound according to claim 2 wherein said compound is 7β-[D-2-(6,7-dihydroxychromone-3-carboxamido)-2-(4-hydroxyphenyl)acetamido]-3-[(5-methyl-1,3,4-thiadiazol-2-yl)thiomethyl]-3-cephem-4-carboxylic acid or pharmaceutically acceptable salt thereof.

8. A compound according to claim 2 wherein said compound is 7β-[D-2-(6,7-diacetoxychromone-3-carboxamido)-2-phenylacetamido]-3-[(1-methyltetrazol-5-yl)thiomethyl]-3-cephem-4-carboxylic acid or pharmaceutically acceptable salt thereof.

9. A compound according to claim 2 wherein said compound is 7β-[D-2-(6,7-diacetoxychromone-3-carboxamido)-2-phenylacetamido]-3-[(5-methyl-1,3,4-thiadiazol-2-yl)thiomethyl]-3-cephem-4-carboxylic acid or pharmaceutically acceptable salt thereof.

10. A compound according to claim 2 wherein said compound is 7β-[D-2-(6,7-diacetoxychromone-3-carboxamido)-2-(4-hydroxyphenyl)acetamido]-3-[(1-methyltetrazol-5-yl)-thiomethyl]-3-cephem-carboxylic acid or pharmaceutically acceptable salt thereof.

11. A compound according to claim 2 wherein said compound is 7β-[D-2-(6,7-diacetoxychromone-3-carboxamido)-2-(4-hydroxyphenyl)acetamido]-3-[(5-methyl-1,3,4-thiadiazol-2-yl)thiomethyl]-3-cephem-carboxylic acid or pharmaceutically acceptable salt thereof.

12. A compound according to claim 2 wherein said compound is 7β-[D-2-(7,8-dihydroxychromone-3-carboxamido)-2-(4-hydroxyphenyl)acetamido]-3-[(1-methyltetrazol-5-yl)-thiomethyl]-3-cephem-4-carboxylic acid or pharmaceutically acceptable salt thereof.

13. A compound according to claim 2 wherein said compound is 7β-[D-2-(7,8-diacetoxychromone-3-carboxamido)-2-phenylacetamido]-3-[(5-methyl-1,3,4-thiadiazol-2-yl)thiomethyl]-3-cephem-4-carboxylic acid or pharmaceutically acceptable salt thereof.

14. A compound according to claim 2 wherein said compound is 7β-[D-2-(7,8-diacetoxychromone-3-carboxamido)-2-(4-hydroxyphenyl)-acetamido]-3-[(1-methyltetrazol-5-yl)-thiomethyl]-3-cephem-4-carboxylic acid or pharmaceutically acceptable salt thereof.

15. A compound according to claim 2 wherein said compound is 7β-[D-2-(7,8-diacetoxychromone-3-carboxamido)-2-(4-hydroxyphenyl)acetamido]-3-[(5-methyl-1,3,4-thiadiazol-2-yl)thiometyl]-3-cephem-4-carboxylic acid or pharmaceutically acceptable salt thereof.

16. A compound according to claim 3 wherein said compound is 7β-[D-2-(6,7-dihydroxychromone-3-carboxamido)-2-(4-hydroxyphenyl)acetamido]-3-[(1-carboxymethyltetrazol-5-yl)thiomethyl]-3-cephem-4-carboxylic acid or pharmaceutically acceptable salt thereof.

17. A compound according to claim 3 wherein said compound is 7β-[D-2-(6,7,8-trihydroxychromone-3-carboxamido)-2-(4-hydroxyphenyl)acetamido]-3-[(1-carboxymethyltetrazol-5-yl)thiomethyl]-3-cephem-4-carboxylic acid or pharmaceutically acceptable salt thereof.

18. An antibacterial composition which comprises an antibacterially effective amount of a cephalosporin compound of the formula

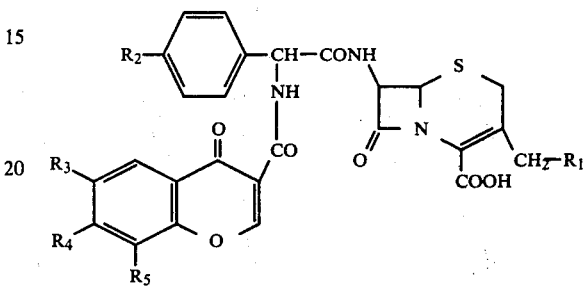

wherein R₁ represents a nitrogen-containing heterocyclic-thio group, the nitrogen-containing heterocyclic group of which is selected from the group consisting of pyrrolyl, pyridyl and its N-oxide, imidazolyl, pyrazolyl, pyrimidinyl, pyridazinyl, 1H-1,2,4-triazolyl, 4H-1,2,4-triazolyl, 1H-1,2,3-triazolyl, 2H-1,2,3-triazolyl, 1H-tetrazolyl, 2H-tetrazolyl, thiazolyl, 1,2,3-thiadiazolyl, 1,2,4-thiadiazolyl, 1,3,4-thiadiazolyl, oxazolyl, 1,3,4-oxadiazolyl, 1,2,5-oxadiazolyl, morpholino, benzothiazolyl and benzoxazolyl, said heterocyclic groups being unsubstituted or substituted by methyl, ethyl, propyl, isopropyl, amino, dimethylaminoethyl, dimethylaminomethyl, diethylaminoethyl, carboxymethyl or carboxyethyl, R₂ represents hydrogen or hydroxy, and R₃, R₄ and R₅ each represents hydrogen, hydroxy, acetoxy, propionyloxy or benzyloxy or a pharmaceutically acceptable salt thereof and a pharmaceutically acceptable carrier therefor.

* * * * *